US006197543B1

(12) United States Patent
Hillman et al.

(10) Patent No.: US 6,197,543 B1
(45) Date of Patent: Mar. 6, 2001

(54) HUMAN VESICLE MEMBRANE PROTEIN-LIKE PROTEINS

(75) Inventors: Jennifer L. Hillman, Mountain View; Henry Yue, Sunnyvale; Neil C. Corley, Mountain View; Preeti Lal; Purvi Shah, both of Sunnyvale, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 08/959,004

(22) Filed: Oct. 28, 1997

(51) Int. Cl.[7] ............................ C12P 21/06; C07H 17/00; C07K 14/00

(52) U.S. Cl. .................. 435/69.1; 435/253.2; 435/320.1; 435/325; 536/23.1; 530/350

(58) Field of Search ........................ 536/23.1; 435/69.1, 435/320.1, 325, 253.2; 530/350

(56) References Cited

PUBLICATIONS

Kaldi et al. FEBS Lett. 315(3):217–222, Jan. 1993.*
Zwacka et al. Embo J. 13(21):5129–5134, 1994.*
Database ENBL, Entry Emest8:HS1321528, Accession No. AA531555, Jul. 24, 1997, 99% identity with Seq.ID:2 nt.452–901 reverse orientation.
Database EMBL, Entry Emest1:AA600701, Accession No. AA600701, Sep. 29, 1997, 98% identity with Seq.ID:2 nt.538–993 reverse orientation.
Database EMBL, Entry Emest9:HS215293, Accession No. N42215, Jan. 27, 1996, 97% identity with Seq.ID:2 nt.324–839.
Database EMBL, Entry Emest9:HS467300, Accession No. N68467, Mar. 14, 1996, 98% identity with Seq.ID:2 nt.547–993 reverse orientation.
Holzinger, A. et al., "cDNA Cloning and mRNA Expression of the Human Adrenoleukodystrophy Related Protein (ALDRP), a Peroxisomal ABC Transporter", *Biochemical and Biophysical Research Communictions,* 239: 261–264 (1997).
Mosser, J. et al., "The gene responsible for adrenoleukodystrophy encodes a peroxisomal membrane protein", *Human Molecular Genetics,* 3: 265–271 (1994).
Holzinger, A. et al., "Primary Structure of Human PMP69, a Putative Peroxisomal ABC–Transporter", *Biochemical and Biophysical Research Communications,* 237: 152–157 (1997).
Kamijo, E. et al., "The 70–kDa Peroxisomal Membrane Protein Is a Member of the Mdr (P–glycoprotein)–related ATP–binding Protein Superfamily", *The Journal of Biological Chemistry,* 265: 4534–4540 (1990).
deDuve, Christian, "The Peroxisome in Retrospect" *Annals N.Y.Acad.Sci.* (1996) 804:1–10.

Hunziker, W. and Geuze, H.J., "Intracellular trafficking of lysosomal membrane proteins" *BioEssays* (1996) 18:379–389.
Singer–Kruger, B. et al., "Partial Purification and Characterization of Early and Late Endosomes from Yeast" *J.Biol.Chem.* (1993) 268:14376–14386.
Stamnes, M.A. et al., "An integral membrane component of coatomer–coated transport vesicles defines a family of proteins involved in budding" *Proc.Natl.Acad.Sci.USA* (1995) 92:8011–8015.
Nagase, T. et al., "Prediction of the Coding Sequences of Unidentified Human Genes. VI. The Coding Sequences of 80 New Genes (KIAA0201–KIAA0280) Deduced by Analysis of cDNA Clones from Cell Line KG–1 and Brain" *DNA Res.* (1996) 3:321–329.
Rothman, J.E. and Wieland, F.T. "Protein Sorting by Transport Vesicles" *Science* (1996) 272:227–234.
Mayer, R.J. et al., "Endosome–Lysosomes, Ubiquitin and Neurodegeneration" *Adv.Exp.Med.Biol.* (1996) 389:261–269.
Waterham, H.R. and Cregg, J.M. "Peroxisome biogenesis" *BioEssays* (1996) 19:57–66.
Moser, H.W. and Moser, A.B. "Peroxisomal Disorders: Overview" *Annals N.Y.Acad.Sci.* (1996) 804:1–10.
Dodt, G. et al., "From Expressed Sequence Tags to Perosisome Biogenesis Disorder Genes" *Ann.NY Acad.Sci.* (1996) 804:516–523.
Kaneko, T. et al., "Sequence Analysis of the Genome of the Unicellular *Cyanobacterium Synechocystis* sp. strain PCC6803. II. Sequence Determination of the Entire Genome and Assignment of Potential Protein–Coding Regions." *DNA Res.* (1996) 30:109–136.
Garrard, L.J. and Goodman, J.M. "Two Genes Encode the Major Membrane–Associated Protein of Methanol–Induced Peroxisomes from *Candida Boidinii*"*J.Biol.Chem.* (1989) 264:13929–13937.
Tomilin, N. and Doerfler, W. (GI 1773069), GenBank Sequence Database (Accession U82614), National Center for Biotechnology Information, National Library of Medicine, Bethesda, Maryland, 20894.
Santos, M.J. et al., "Characterization of Human Peroxisomal Membrane Proteins" *J.Biol.Chem.* (1994) 269:24890–24896.
Gartner, J. et al., "The 22–kD Peroxisomal Integral Membrane Protein in Zellweger Syndrome—Presence, Abundance, and Association with a Peroxisomal Thiolase Precursor Protein" *Pediatr.Res.* (1991) 29:141–146.

(List continued on next page.)

*Primary Examiner*—Karen Cochrane Carlson
(74) *Attorney, Agent, or Firm*—Incyte Genomics, Inc.

(57) ABSTRACT

The invention provides three human vesicle membrane protein-like proteins (VMP) and polynucleotides which identify and encode VMP. The invention also provides expression vectors, host cells, agonists, antibodies, and antagonists. The invention also provides methods for treating and preventing disorders associated with expression of VMP.

14 Claims, 22 Drawing Sheets

OTHER PUBLICATIONS

Kaneko, T. et al., (GI 1652844), GenBank Sequence Database (Accession D90909; AB001339), National Center for Biotechnology Information, National Library of Medicine, Bethesda, Maryland, 20894.

Nomura, N. (GI 1665776), GenBank Sequence Database (Accession D87444), National Center for Biotechnology Information, National Library of Medicine, Bethesda, Maryland, 20894.

Singer–Kruger, B. et al., (GI 2131246), GenBank Sequence Database (Accession S64915), National Center for Biotechnology Information, National Library of Medicine, Bethesda, Maryland, 20894.

Schimmoeller, F. et al., (GI 1737489), GenBank Sequence Database (Accession U81006), National Center for Biotechnology Information, National Library of Medicine, Bethesda, Maryland, 20894.

* cited by examiner

```
            9      18      27       36      45      54
GTC GCC GCT GTG CCG CTA GCG GTG CCC CGC CTG CGG TGG CAC CAG CCA GGA 63      72      81       90      99     108
GGG CCG GGA AGT TGG GGA AAG GTT GGG GCC CGG TTG AGN GGG NCG GGT TTA 117     126     135      144     153     162
AAT TTG GGG GGC GGC CCA GGC CCT TCC GCA GGG TGT CGC TGT GCC GCT 171     180     189      198     207     216
AGC GGT GCC CCG CCT GCT GCG GTG GCA CCA GCC AGG AGG CGG AGT GGA AGT GGC 225     234     243      252     261     270
CGT GGG GCG GGT ATG GGA CTA GCT GGC GTG TGC GCC CTG AGA CGC TCA GCG GGC
             M   G   L   A   G   V   C   A   L   R   R   S   A   G 279     288     297      306     315     324
TAT ATA CTC GTC GGT GGG GCC GGC GGT CAG TCT GCG GCA GCG GCA GCA AGA CGG
 Y   I   L   V   G   G   A   G   G   Q   S   A   A   A   A   R   R 333     342     351      360     369     378
TGC AGT GAA GGA GAG TGG GCG GCC GGC GGG GTC TCT GCG CGC AGT TTC AGC GCT
 C   S   E   G   E   W   A   A   G   G   V   S   A   R   S   F   A 387     396     405      414     423     432
GCA GCC ATG GCC CCA ATC AAG GTG GGA GAT GCC ATC CCA GCA GTG GAG GTG TTT
 A   A   M   A   P   I   K   V   G   D   A   I   P   A   V   E   V   F

FIGURE 1A
```

```
       441            450            459            468            477            486
GAA GGG GAG CCA GGG AAC AAG GTG AAC CTG GCA GAG CTG TTC AAG GGC AAG AAG
 E   G   E   P   G   N   K   V   N   L   A   E   L   F   K   G   K   K 495            504            513            522            531            540
GGT GTG CTG TTT GGA GTT CCT GGG GCC TTC ACC CCT GGA TGT TCC AAG ACA CAC
 G   V   L   F   G   V   P   G   A   F   T   P   G   C   S   K   T   H 549            558            567            576            585            594
CTG CCA GGG TTT GTG GAG CAG GCT GAG GCT CTG AAG GCC AAG GGA GTC CAG GTG
 L   P   G   F   V   E   Q   A   E   A   L   K   A   K   G   V   Q   V 603            612            621            630            639            648
GTG GCC TGT CTG AGT GTT AAT GAT GCC TTT GTG ACT GGC TGG GGC GAG CGA GCC
 V   A   C   L   S   V   N   D   A   F   V   T   G   W   G   E   R   A 657            666            675            684            693            702
CAC AAG GCG GAA GGC AAG GTT CGG CTC CTG GCT GAT CCC ACT GGG GCC TTT GGG
 H   K   A   E   G   K   V   R   L   L   A   D   P   T   G   A   F   G 711            720            729            738            747            756
AAG GAG ACA GAC TTA CTA GAT TCG CTG TCC ATC GTG GTG TCC ATC TTT GGG AAT CGA
 K   E   T   D   L   L   D   S   L   S   I   V   V   S   I   F   G   N   R 765            774            783            792            801            810
CGT CTC AAG AGG TTC TCC ATG GTA CAG GAT GGC ATA GTG AAG GCC CTG AAT
 R   L   K   R   F   S   M   V   Q   D   G   I   V   K   A   L   N
```

FIGURE 1B

```
     819         828         837         846         855         864
GTG GAA CCA GAT GGC ACA GGC CTC ACC TGC AGC CTG GCA CCC AAT ATC ATC TCA
 V   E   P   D   G   T   G   L   T   C   S   L   A   P   N   I   I   S 873         882         891         900         909         918
CAG CTC TGA GGC CCT GGG CCA GAT TAC TTC CTC CAC CCC TCC CTA TCT CAC CTG
 Q   L 927         936         945         954         963         972
CCC AGC CCT GTG CTG GGG CCC TGC AAT TGG AAT GTT GGC CAG ATT TCT GCA ATA 981         990
AAC ACT TGT GGT TTG CGG CCA
```

FIGURE 1C

```
                                                        9          18          27          36          45          54
                                                    G  GTG  CCC  GCA  CGG  CGC  TGC  GGC  TCG  AGG  GAG  GCG  ATG  GCG  CCG  GCC
                                                                                                           M    A    P    A
     63          72          81          90          99         108
GCG  TCC  AGG  CTG  CGG  GCC  GAA  GCC  GGG  CTC  GGG  GCG  CTG  CCG  CGG  GCG  CTC
  A    S    R    L    R    A    E    A    G    L    G    A    L    P    R    A    L
    117         126         135         144         153         162
GCC  CAG  TAC  TTG  CTC  TTC  CTG  CGG  CTC  TAC  CCG  GTG  CTG  CTC  ACC  AAG  GCG  ACC
  A    Q    Y    L    L    F    L    R    L    Y    P    V    L    L    T    K    A    T
    171         180         189         198         207         216
AGT  GGC  ATT  TTG  TCA  GCA  CTT  GGG  CTT  GGG  AAC  TTC  CTG  GCC  CAG  ATG  ATT  GAG  AAG  AAG
  S    G    I    L    S    A    L    G    L    G    N    F    L    A    Q    M    I    E    K    K
    225         234         243         252         261         270
CGG  AAA  AAA  GAA  AAC  TCT  AGA  AGT  CTG  GAT  GTC  GGT  GGG  CCT  CTG  AGA  TAT  GCC
  R    K    K    E    N    S    R    S    L    D    V    G    G    P    L    R    Y    A
    279         288         297         306         315         324
GTT  TAC  GGG  TTC  TTC  ACA  GGG  CCG  CTG  AGT  CAC  TTC  TAC  TTC  TTC  ATG
  V    Y    G    F    F    T    G    P    L    S    H    F    Y    F    F    M
    333         342         351         360         369         378
GAA  CAT  TGG  ATC  CCT  GAG  GTC  CCC  CTG  GCA  GGG  CTC  AGG  CTT  CTC  CTG
  E    H    W    I    P    E    V    P    L    A    G    L    R    L    L    L
```

FIGURE 2A

```
387            396            405            414            423            432
GAC CGC CTC GTC TTT GCA CCG GCC TTC CTC ATG TTG TTC TTC CTC ATC ATG AAC
 D   R   L   V   F   A   P   A   F   L   M   L   F   F   L   I   M   N 441            450            459            468            477            486
TTT CTG GAG TTC CGG GTG CTC TTC GCC AAC CTG GCA GCT CTG TTC TGG TAT GCC
 F   L   E   F   R   V   L   F   A   N   L   A   A   L   F   W   Y   A 495            504            513            522            531            540
TAC CTG GCC TCC TTG GGG AAG TGA CGA CCG CTG GGA GAA CAT CAG GTG CAC TGT
 Y   L   A   S   L   G   K 549            558            567            576            585            594
GGA CGT GGG TCT GGG GGT CTC ACC CGC CCA GCG AGA GCA GAA CCA ATC CAG TCA 603            612            621            630            639            648
GGA TGT CAC TGA CTC TAA ATC AGG TGA TTC AAG ATG CCC CAA AAA TGA TGG ATA 657            666            675            684            693            702
GAG AAA CAG AAA TCT CTG AAT GTC AGA AAC CCT GTC TTT TAA AAA GGC AGT CAC 711            720            729            738            747            756
TGC CTT CAG GTG GTG CTG CCC CAG AAA CTT AAA ATT TAG TCG AGG CAG TTT CAA 765            774            783            792            801
TTG TTA CTG TGG ACC GAA TTA GGA TCA CAA TAA ACG ATA ATG GGT C
```

```
              9         18        27        36        45        54
G   TTG  CGG  TCC  GCT  TCG  GTT  TCT  GCG  GGA  CCC  GGG  GTG  TCT  CCT  AGC  GCA 63        72        81        90        99        108
ACC GGA  ACT  AGC  CTT  CTG  GGG  GCC  TTC  CTT  TAT  CTC  TGG  CGG  CCT  TGT  AGT 117       126       135       144       153       162
CGT CTC  CGA  GAC  TCC  CCA  CCC  CTC  TTT  CCC  TCT  TGA  CCC  CCT  AGG  TTT  GAT  TGC 171       180       189       198       207       216
CCT TTC  GAA  ACA  ACT  ATC  ATG  AGC  GCG  AGG  CTG  CCG  GTG  TTG  TCT  CCA  CCT
                             M    S    A    R    L    P    V    L    S    P    P 225       234       243       252       261       270
CGG CCG  CGG  CTG  TTG  CTG  TCG  CTG  CTC  CTG  GGG  GCG  GTT  CCT  GGC
R   P    R    L    L    L    S    L    L    L    G    A    V    P    G 279       288       297       306       315       324
CCG CGG  AGC  GGC  GCT  TTC  TAC  CTG  CCC  GGC  CTG  GCG  CCC  GTC  AAC  TTC  TGC
P   R    S    G    A    F    Y    L    P    G    L    A    P    V    N    F    C 333       342       351       360       369       378
GAC GAA  AAA  AAG  AGC  TGC  GAG  GAC  GAG  AAG  GCC  GAA  ATA  GAA  TAC  ACA  TTT  GTG  AAC
D   E    K    K    S    C    E    D    E    K    A    E    I    E    Y    T    F    V    N 387       396       405       414       423       432
AGA CTT  GAT  TCA  GTG  GAA  TCA  GTT  CTT  CCT  TAT  GAA  TAC  ACA  GCG  TTT  GAT  TTT
R   L    D    S    V    E    S    V    L    P    Y    E    Y    T    A    F    D    F
```

```
      441        450        459        468        477        486
TGC CAA GCA TCA GAA GGA AAG CGC GAA TCT CCA AAT CTT GGT CAG GTA CTA TTC
 C   Q   A   S   E   G   K   R   E   S   P   N   L   G   Q   V   L   F 495        504        513        522        531        540
GGG GAA AGA ATT GAA CCT TCA CCA TAT AAG TTT ACG AAT AAG AAG GAG ACC
 G   E   R   I   E   P   S   P   Y   K   F   T   N   K   K   E   T 549        558        567        576        585        594
TGT AAG CTT GTT TGT ACA AAA ACA TAC CAT ACA GAG AAA GAA GAC AAA CAA
 C   K   L   V   C   T   K   T   Y   H   T   E   K   E   D   K   Q 603        612        621        630        639        648
AAG TTA GAA TTC TTG AAA AAA AGC ATG TTA TTG AAT TAT CAA CAT CAC TGG ATT
 K   L   E   F   L   K   K   S   M   L   L   N   Y   Q   H   H   W   I 657        666        675        684        693        702
GTG GAT AAT ATG CCT GTA ACG TGG TGT TAC GAT GTT GAA GAT GGT CAG AGG TTC
 V   D   N   M   P   V   T   W   C   Y   D   V   E   D   G   Q   R   F 711        720        729        738        747        756
TGT AAT CCT GGA TTT CCT ATT GGC TGT TAC ATT ACA GAT AAA GCA TTC GCA AAA
 C   N   P   G   F   P   I   G   C   Y   I   T   D   K   G   H   A   K 765        774        783        792        801        810
GAT GCC TGT GTT ATT AGT TCA GAT TTC CAT GAA AGA GAT ACA TTT TAC ATC TTC
 D   A   C   V   I   S   S   D   F   H   E   R   D   T   F   Y   I   F
```

FIGURE 3B

```
              819             828         837         846         855         864
AAC CAT GTT GAC ATC AAA ATA TAC TAT CAT GTT GAA ACT GGG TCC ATG GGA
 N   H   V   D   I   K   I   Y   Y   H   V   E   T   G   S   M   G 873             882         891         900         909         918
GCA AGA TTA GTG GCT AAA CTT GAA CCG AAA AGC TTC AAA CAT ACC CAT ATA
 A   R   L   V   A   K   L   E   P   K   S   F   K   H   T   H   I 927             936         945         954         963         972
GAT AAA CCA GAC TGC TCA GGG CCC ATG GAC ATA AGT AAC AAG GCT TCT GGG
 D   K   P   D   C   S   G   P   M   D   I   S   N   K   A   S   G 981             990         999        1008        1017        1026
GAG ATA AAA ATT GCC TAT ACT TCT GTT AGC TTC GAG GAA GAT GAT AAG ATC
 E   I   K   I   A   Y   T   S   V   S   F   E   E   D   D   K   I 1035            1044        1053        1062        1071        1080
AGA TGG GCG TCT AGA TGG GAC TAT ATT CTG GAG TCT ATG CCT CAT ACC CAC ATT
 R   W   A   S   R   W   D   Y   I   L   E   S   M   P   H   T   H   I 1089            1098        1107        1116        1125        1134
CAG TGG TTT AGC ATT ATG AAT TCC CTG GTC ATT GTT CTC TTC TTA TCT GGA ATG
 Q   W   F   S   I   M   N   S   L   V   I   V   L   F   L   S   G   M 1143            1152        1161        1170        1179        1188
GTA GCT ATG ATT ATG TTA CGG ACA CTG CAC AAA GAT ATT GCT AGA TAT AAT CAG
 V   A   M   I   M   L   R   T   L   H   K   D   I   A   R   Y   N   Q
```

FIGURE 3C

```
              1197            1206            1215            1224            1233            1242
ATG GAC TCT ACG GAA GAT GCC CAG GAA GAA TTT GGC TGG AAA CTT GTT CAT GGT
 M   D   S   T   E   D   A   Q   E   E   F   G   W   K   L   V   H   G 1251            1260            1269            1278            1287            1296
GAT ATA TTC CGT CCT CCA AGA AAA GGG ATG CTG CTA TCA GTC TTT CTA GGA TCC
 D   I   F   R   P   P   R   K   G   M   L   L   S   V   F   L   G   S 1305            1314            1323            1332            1341            1350
GGG ACA CAG ATT TTA ATT ATG ACC TTT GTG ACT CTA TTT TTC GCT TGC CTG GGA
 G   T   Q   I   L   I   M   T   F   V   T   L   F   F   A   C   L   G 1359            1368            1377            1386            1395            1404
TTT TTG TCA CCT GCC AAC CGA GGA GCG CTG ATG ACG TGT GCT GTG GTC CTG TGG
 F   L   S   P   A   N   R   G   A   L   M   T   C   A   V   V   L   W 1413            1422            1431            1440            1449            1458
GTG CTG CTG GGC ACC CCT GCA GGC TAT GTT GCT GCC AGA TTC TAT AAG TCC TTT
 V   L   L   G   T   P   A   G   Y   V   A   A   R   F   Y   K   S   F 1467            1476            1485            1494            1503            1512
GGA GGT GAG AAG TGG AAA ACA AAT GTT TTA TTA ACA TCA TTT CTT TGT CCT GGG
 G   G   E   K   W   K   T   N   V   L   L   T   S   F   L   C   P   G 1521            1530            1539            1548            1557            1566
ATT GTA TTT GCT GAC TTC TTT ATA ATG AAT CTG ATC CTC TGG GGA GAA GGA TCT
 I   V   F   A   D   F   F   I   M   N   L   I   L   W   G   E   G   S
```

FIGURE 3D

```
                            1575            1584            1593            1602            1611            1620
TCA GCA GCT ATT CCT TTT GGG ACA CTG GTT GCC ATA TTG GCC CTT TGG TTC TGC
 S   A   A   I   P   F   G   T   L   V   A   I   L   A   L   W   F   C 1629            1638            1647            1656            1665            1674
ATA TCT GTG CCT CTG ACG TTT ATT GGT GCA TAC TTT GGT TTT AAG AAG AAT GCC
 I   S   V   P   L   T   F   I   G   A   Y   F   G   F   K   K   N   A 1683            1692            1701            1710            1719            1728
ATT GAA CAC CCA GTT CGA ACC AAT CAG ATT CCA CGT CAG ATT CCT GAA CAG TCG
 I   E   H   P   V   R   T   N   Q   I   P   R   Q   I   P   E   Q   S 1737            1746            1755            1764            1773            1782
TTC TAC ACG AAG CCC TTG CCT GGT ATT ATC ATG GGA GGG ATT TTG CCC TTT GGC
 F   Y   T   K   P   L   P   G   I   I   M   G   G   I   L   P   F   G 1791            1800            1809            1818            1827            1836
TGC ATC TTT ATA CAA CTT TTC TTC ATT CTG AAT AGT ATT TGG AAT AGT ATG
 C   I   F   I   Q   L   F   F   I   L   N   S   I   W   S   I   Q   M 1845            1854            1863            1872            1881            1890
TAT TAC ATG TTT GGC TTC CTA TTT CTG GTG TTT ATT TTG GTT ATT ACC TGT
 Y   Y   M   F   G   F   L   F   L   V   F   I   L   V   I   T   C 1899            1908            1917            1926            1935            1944
TCT GAA GCA ACT ATA CTT TGC TAT TTC CAC CTA TGT GCA GAG GAT TAT CAT
 S   E   A   T   I   L   C   Y   F   H   L   C   A   E   D   Y   H
```

FIGURE 3E

```
      1953            1962            1971            1980            1989            1998
TGG CAA TGG CGT TCA TTC CTT ACG AGT GGC TTT ACT GCA GTT TAT TTC TTA ATC
 W   Q   W   R   S   F   L   T   S   G   F   T   A   V   Y   F   L   I 2007            2016            2025            2034            2043            2052
TAT GCA GTA CAC TAC TTC TTT TCA AAA CTG CAG ATC ACG GGA ACA GCA AGC ACA
 Y   A   V   H   Y   F   F   S   K   L   Q   I   T   G   T   A   S   T 2061            2070            2079            2088            2097            2106
ATT CTG TAC TTT GGT TAT ACC ATG ATA ATG GTT TTG ATC TTC TTT CTT TTT ACA
 I   L   Y   F   G   Y   T   M   I   M   V   L   I   F   F   L   F   T 2115            2124            2133            2142            2151            2160
GGA ACA ATT GGC TTC TTT GCA TGC TTT TGG TTT GTT ACC AAA ATA TAC AGT GTG
 G   T   I   G   F   F   A   C   F   W   F   V   T   K   I   Y   S   V 2169            2178            2187            2196            2205            2214
GTG AAG GTT GAC TGA AGA AGT CCA GTG TGT CCA GTT AAA ACA GAA ATA AAT TAA
 V   K   V   D 2223            2232            2241            2250            2259            2268
ACT CTT CAT CAA CAA AGA CCT GTT TTT GTG ACT GCC TTG AGT TTT ATC AGA ATT 2277            2286            2295            2304            2313            2322
ATT GGC CTA GTA ATC CTT CAG AAA CAC CGT AAT TCT AAA TAA ACC TCT TCC CAT
```

FIGURE 3F

```
                    2331                2340                2349                2358                2367                2376
ACA CCT TTC CCC CAT AAG ATG TGT CTT CAA CAC TAT AAA GCA TTT GTA TTG TGA 2385                2394                2403                2412                2421                2430
TTT GAT TAA GTA TAT ATT TGG TTG TTC TCA ATG AAG AGC AAA TTT AAA TAT TAT 2439                2448                2457                2466                2475                2484
GTG CAT TTG TAA ATA CAG TAG CTA TAA AAT TTT CCA TAC TTC TAA TGG CAG AAT 2493                2502                2511                2520                2529                2538
AGA GGA GGC CAT ATT AAA TAA TAC TGA TGA AAG GCA GGA CAC TGC ATT GTA AAT 2547                2556                2565                2574                2583                2592
AGG ATT TTC TAG GCT CGG TAG GCA GAA AGA ATT ATT TTT CTT TGA AGG AAA TAA 2601                2610                2619                2628                2637                2646
CTT TTT ATC ATG GTA ATT TTG AAG GAT GAT TCC TAT GAT GTG TTC ACC AGG GGA 2655                2664                2673                2682                2691                2700
ATG TGG CTT TTA AAG AAA ATC TTC TTA TTC CCA TGG TTG TAA CTG TTC ATA TCT TAC 2709                2718                2727                2736                2745                2754
TTT TCT GTG TTG ACT TCA TTA TTC TCA TGG TAT TGG CCT TTT AAA CTA TGT GCC 2763                2772                2781                2790                2799
TCT GAG TCT TTC AAT TTA TAA ATT TGT TAT AAT AAA TAT TAT AAA AAT GA
```

HUMAN VESICLE MEMBRANE PROTEIN-LIKE PROTEINS

FIELD OF THE INVENTION

This invention relates to nucleic acid and amino acid sequences of three human vesicle membrane protein-like proteins and to the use of these sequences in the diagnosis, prevention, and treatment of developmental, vesicle trafficking, immunological, reproductive, and neoplastic disorders.

BACKGROUND OF THE INVENTION

Eukaryotic organisms are distinct from prokaryotes in possessing many intracellular organelle structures. Many of the metabolic reactions which separate eukaryotic biochemistry from prokaryotic biochemistry take place within these structures. In particular, many cellular functions require very strict reagent conditions, and the organelles enable compartmentalization and isolation of reactions which might otherwise cripple cytosolic metabolic processes.

Isolation of intracellular organelles from rat liver has demonstrated the presence of two distinct organelles, the lysosome and the peroxisome (de Duve, C. (1996) Ann. N.Y. Acad. Sci. 804:1–10). Lysosomes are the site of degradation of obsolete intracellular material during autophagy and of extracellular molecules following endocytosis and phagocytosis. They are derived from endosomes, which in turn are formed from budding of the trans-Golgi network (TGN) or from clathrin-coated membrane vesicles invaginating from the plasma membrane. Lysosomes contain hydrolytic enzymes, and the enveloping membranes of lysosomes and early/late endosomes are enriched in highly glycosylated transmembrane proteins of largely unknown function. Some lysosomal membrane proteins follow the constitutive secretory pathway and reach lysosomes indirectly via the cell surface. Other membrane proteins exit the TGN in clathrin-coated vesicles for direct delivery to endosomes and to lysosomes (Hunziker, W. and Geuze, H. J. (1996) BioEssays 18:379–389).

Genetic studies in yeast and biochemical studies in animal cells have provided evidence that the endocytic pathways and protein sorting in all eukaryotes probably share common enzymes and membrane components. An endocytic endosomal intermediate is responsible for the transport of the pheromone alpha-factor from the plasma membrane to the vacuole of the yeast, Saccharomyces cerevisiae. Proteins of the yeast endosomal membrane which may contribute to the transport of alpha-factor have been investigated in some detail. In particular, a protein with ten potential transmembrane domains, the EMP70 (p24a) precursor, has been identified (Singer-Kruger, B. et al. (1993) J. Biol. Chem. 268:14376–14386). Electron microscopic examination of yeast cells lacking functional EMP70 (p24a) shows a decrease in steady state vesicle accumulation and this suggests that EMP70 (p24a) is necessary for efficient vesicle budding (Stamnes, M. A. et al. (1995) Proc. Natl. Acad. Sci. 92:8011–8015). A similar protein, KIAA0255, has been identified in a human myoblast cell line (Nagese, T. et al. (1996) DNA Res. 3:321–329).

Protein sorting by transport vesicles, such as the endosome, has important consequences for a variety of physiological processes including cell surface growth, the biogenesis of distinct intracellular organelles, endocytosis, and the controlled release of hormones and neurotransmitters (Rothman, J. E. and Wieland, F. T. (1996) Science 272:227–234). In particular, neurodegenerative disorders and other neuronal pathologies are associated with biochemical flaws during endosomal protein sorting or endosomal biogenesis (Mayer R. J. et al. (1996) Adv. Exp. Med. Biol. 389:261–269).

The peroxisome is the site of many important metabolic reactions in eukaryotes such as lipid metabolism and gluconeogenesis, and is thought to cooperate intimately in biochemical reactions with the chloroplast (in plants and some protists) and the mitochondrion (in protists, animals, and plants). Peroxisomes are independent organelles and are not members of the secretory pathway family of organelles. They are characterized by a single membrane and a finely granulated matrix and are the site of many peroxide-generating oxidative reactions in the cell. Peroxisomes are unique among eukaryotic organelles in that their size, number, and enzyme content vary depending upon organism, cell type, and metabolic needs. Assembly of peroxisomes and their contents within the cell is termed biogenesis. Perixosome biogenesis can be divided into the following specific tasks: (1) membrane lipid acquisition, (2) proliferation/replication, (3) segregation, and (4) protein import. The majority of peroxisome-associated proteins are membrane-bound or are found proximal to the cytosolic or the lumenal side of the peroxisome membrane (Waterham, H. R. and Cregg, J. M. (1996) BioEssays 19:57–66).

Genetic defects in peroxisome proteins which result in peroxisomal deficiencies have been linked to a number of human pathologies, including Zellweger syndrome, rhizomelic chonrodysplasia punctata, X-linked adrenoleukodystrophy, acyl-CoA oxidase deficiency, bifunctional enzyme deficiency, classical Refsum's disease, DHAP alkyl transferase deficiency, and acatalasemia (Moser, H. W. and Moser, A. B. (1996) Ann. NY Acad. Sci. 804:427–441). Some of these peroxisome proteins are required for intracellular assembly of the organelle, including PAF-1, PXR1, and PXAA1 (Dodt, G. et al. (1996) Ann. N.Y. Acad. Sci. 804:516–523). Membrane protein homologs and their cDNA counterparts have been isolated from many organisms including the cyanobacterium Synechocystis (s111621), Candida boidinii (PMP20), and rat (peroxisomal 22 kDa membrane protein, PMP22) (Kaneko, T. et al. (1996) DNA Res. 3:109–136; Garrard, L. J. and Goodman, J. M. (1989) J. Biol. Chem. 264:13929–13937; and Kaldi, K. et al. (1993) FEBS Lett. 315:217–222). An mRNA which has some homology with peroxisome membrane proteins is down-regulated in adenovirus 5-infected HeLa cells (DRAV5; Tomilin, N. and Doerfler, W. (1997) GenBank GI 1773069). Peroxisomal membrane proteins isolated from human liver include two integral membrane proteins of 22 kDa and 17 kDa (Santos, M. J. et al. (1994) J. Biol. Chem. 269:24890–24896). In addition, Gartner, J. et al. (1991; Pediatr. Res. 29:141–146) found a 22 kDa integral membrane protein associated with lower density peroxisome-like subcellular fractions in patients with Zellweger syndrome.

The discovery of three new human vesicle membrane protein-like proteins and the polynucleotides encoding them satisfies a need in the art by providing new compositions which are useful in the diagnosis, prevention, and treatment of developmental, vesicle trafficking, immunological, reproductive, and neoplastic disorders.

SUMMARY OF THE INVENTION

The invention features three substantially purified polypeptides, human vesicle membrane protein-like proteins (designated collectively as "VMP" and individually as "VMP1", "VMP2", and "VMP3"), having the amino acid sequences shown in SEQ ID NO:1, SEQ ID NO:3, or SEQ ID NO:5, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding VMP1 under conditions suitable for the expression of the polypeptide; and b) recovering the polypeptide from the host cell culture.

The invention also provides a pharmaceutical composition comprising a substantially purified VMP1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for treating or preventing a developmental disorder comprising administering to a subject in need of such treatment an effective amount of a pharmaceutical composition comprising purified VMP1.

The invention also provides a method for treating or preventing a vesicle trafficking disorder comprising administering to a subject in need of such treatment an effective amount of a pharmaceutical composition comprising purified VMP1.

The invention also provides a method for treating or preventing an immunological disorder comprising administering to a subject in need of such treatment an effective amount of an antagonist to VMP1.

The invention also provides a method for treating or preventing a reproductive disorder comprising administering to a subject in need of such treatment an effective amount of an antagonist to VMP1.

The invention also provides a method for treating or preventing a neoplastic disorder comprising administering to a subject in need of such treatment an effective amount of an antagonist to VMP1.

The invention also provides a method for detecting a polynucleotide which encodes VMP1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding VMP1 in the biological sample. In one aspect the nucleic acid material of the biological sample is amplified by the polymerase chain reaction prior to hybridization.

The invention further provides an isolated and substantially purified polynucleotide sequence encoding the polypeptide comprising the amino acid sequence of SEQ ID NO:3 or fragments thereof and a composition comprising said polynucleotide sequence. The invention also provides a polynucleotide sequence which hybridizes under stringent conditions to the polynucleotide sequence encoding the amino acid sequence SEQ ID NO:3, or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO:4 or variants thereof In addition, the invention provides a polynucleotide sequence which hybridizes under stringent conditions to the polynucleotide sequence of SEQ ID NO:4. The invention also provides a polynucleotide sequence comprising the complement of SEQ ID NO:4, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3 or a fragment thereof, the method comprising the steps of: a) culturing the host cell containing an expression vector containing at least a fragment of the polynucleotide sequence encoding VMP2 under conditions suitable for the expression of the polypeptide; and b) recovering the polypeptide from the host cell culture.

The invention also provides a pharmaceutical composition comprising a substantially purified VMP2 having the amino acid sequence of SEQ ID NO:3 in conjunction with a suitable pharmaceutical carrier.

The invention also provides a purified antagonist of the polypeptide of SEQ ID NO:3. In one aspect the invention provides a purified antibody which binds to a polypeptide comprising the amino acid sequence of SEQ ID NO:3.

Still further, the invention provides a purified agonist of the polypeptide of SEQ ID NO:3.

The invention also provides a method for treating or preventing a developmental disorder comprising administering to a subject in need of such treatment an effective amount of a pharmaceutical composition comprising purified VMP2.

The invention also provides a method for treating or preventing a vesicle trafficking disorder comprising administering to a subject in need of such treatment an effective amount of a pharmaceutical composition comprising purified VMP2.

The invention also provides a method for treating or preventing an immunological disorder comprising administering to a subject in need of such treatment an effective amount of an antagonist to VMP2.

The invention also provides a method for treating or preventing a reproductive disorder comprising administering to a subject in need of such treatment an effective amount of an antagonist to VMP2.

The invention also provides a method for treating or preventing a neoplastic disorder comprising administering to a subject in need of such treatment an effective amount of an antagonist to VMP2.

The invention also provides a method for detecting a polynucleotide which encodes VMP2 in a biological sample comprising the steps of: a) hybridizing the complement of the polynucleotide sequence which encodes SEQ ID NO:3 to nucleic acid material of a biological sample, thereby forming a hybridization complex; and b) detecting the hybridization complex, wherein the presence of the complex correlates with the presence of a polynucleotide encoding VMP2 in the biological sample. In one aspect the nucleic acid material of the biological sample is amplified by the polymerase chain reaction prior to hybridization.

The invention further provides an isolated and substantially purified polynucleotide sequence encoding the polypeptide comprising the amino acid sequence of SEQ ID NO:5 or fragments thereof and a composition comprising said polynucleotide sequence. The invention also provides a polynucleotide sequence which hybridizes under stringent conditions to the polynucleotide sequence encoding the amino acid sequence SEQ ID NO:5, or fragments of said polynucleotide sequence. The invention further provides a polynucleotide sequence comprising the complement of the polynucleotide sequence encoding the amino acid sequence of SEQ ID NO:5, or fragments or variants of said polynucleotide sequence.

The invention also provides an isolated and purified sequence comprising SEQ ID NO:6 or variants thereof. In addition, the invention provides a polynucleotide sequence which hybridizes under stringent conditions to the polynucleotide sequence of SEQ ID NO:6. The invention also provides a polynucleotide sequence comprising the complement of SEQ ID NO:6, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:5 or a fragment thereof, the method comprising the steps of: a) culturing the host cell containing an expression vector containing at least a fragment of the polynucleotide sequence encoding VMP3 under conditions suitable for the expression of the polypeptide; and b) recovering the polypeptide from the host cell culture.

The invention also provides a pharmaceutical composition comprising a substantially purified VMP3 having the amino acid sequence of SEQ ID NO:5 in conjunction with a suitable pharmaceutical carrier.

The invention also provides a purified antagonist of the polypeptide of SEQ ID NO:5. In one aspect the invention provides a purified antibody which binds to a polypeptide comprising the amino acid sequence of SEQ ID NO:5.

Still further, the invention provides a purified agonist of the polypeptide of SEQ ID NO:5.

The invention also provides a method for treating or preventing a developmental disorder comprising administering to a subject in need of such treatment an effective amount of a pharmaceutical composition comprising purified VMP3.

The invention also provides a method for treating or preventing a vesicle trafficking disorder comprising administering to a subject in need of such treatment an effective amount of a pharmaceutical composition comprising purified VMP3.

The invention also provides a method for treating or preventing an immunological disorder comprising administering to a subject in need of such treatment an effective amount of an antagonist to VMP3.

The invention also provides a method for treating or preventing a reproductive disorder comprising administering to a subject in need of such treatment an effective amount of an antagonist to VMP3.

The invention also provides a method for treating or preventing a neoplastic disorder comprising administering to a subject in need of such treatment an effective amount of an antagonist to VMP3.

The invention also provides a method for detecting a polynucleotide which encodes VMP3 in a biological sample comprising the steps of: a) hybridizing the complement of the polynucleotide sequence which encodes SEQ ID NO:5 to nucleic acid material of a biological sample, thereby forming a hybridization complex; and b) detecting the hybridization complex, wherein the presence of the complex correlates with the presence of a polynucleotide encoding VMP3 in the biological sample. In one aspect the nucleic acid material of the biological sample is amplified by the polymerase chain reaction prior to hybridization.

BRIEF DESCRIPTION OF THE FIGURES

FIGS. 1A, 1B, and 1C show the amino acid sequence (SEQ ID NO:1) and nucleic acid sequence (SEQ ID NO:2) of VMP1. The alignment was produced using MacDNASIS PRO™ software (Hitachi Software Engineering Co. Ltd. San Bruno, Calif.).

FIGS. 2A and 2B show the amino acid sequence (SEQ ID NO:3) and nucleic acid sequence (SEQ ID NO:4) of VMP2. The alignment was produced using MacDNASIS PRO™ software (Hitachi Software Engineering Co. Ltd. San Bruno, Calif.).

FIGS. 3A, 3B, 3C, 3D, 3E, 3F, and 3G show the amino acid sequence (SEQ ID NO:5) and nucleic acid sequence (SEQ ID NO:6) of VMP3. The alignment was produced using MacDNASIS PRO™ software (Hitachi Software Engineering Co. Ltd. San Bruno, Calif.).

FIGS. 4A and 4B show the amino acid sequence alignments among VMP1 (743725; SEQ ID NO:1), *C. boidinii* PMP20 (GI 170899; SEQ ID NO:7), and Synechocystis membrane protein s111621 (GI 1652858; SEQ ID NO:8), produced using the multisequence alignment program of DNASTAR™ software (DNASTAR Inc, Madison Wis.).

FIG. 5 shows the amino acid sequence alignments between VMP2 (1626663; SEQ ID NO:3) and rat PMP22 (GI 297437; SEQ ID NO:9), produced using the multisequence alignment program of DNASTAR™ software (DNASTAR Inc, Madison Wis.).

FIGS. 6A, 6B, 6C, and 6D show the amino acid sequence alignments among VMP3 (2822412; SEQ ID NO:5), human KIAA0255 (GI 1665777; SEQ ID NO:10), and yeast endosome EMP70 (p24a) (GI 2131246; SEQ ID NO:11), produced using the multisequence alignment program of DNASTAR™ software (DNASTAR Inc, Madison Wis.).

DESCRIPTION OF THE INVENTION

Figure 7A:
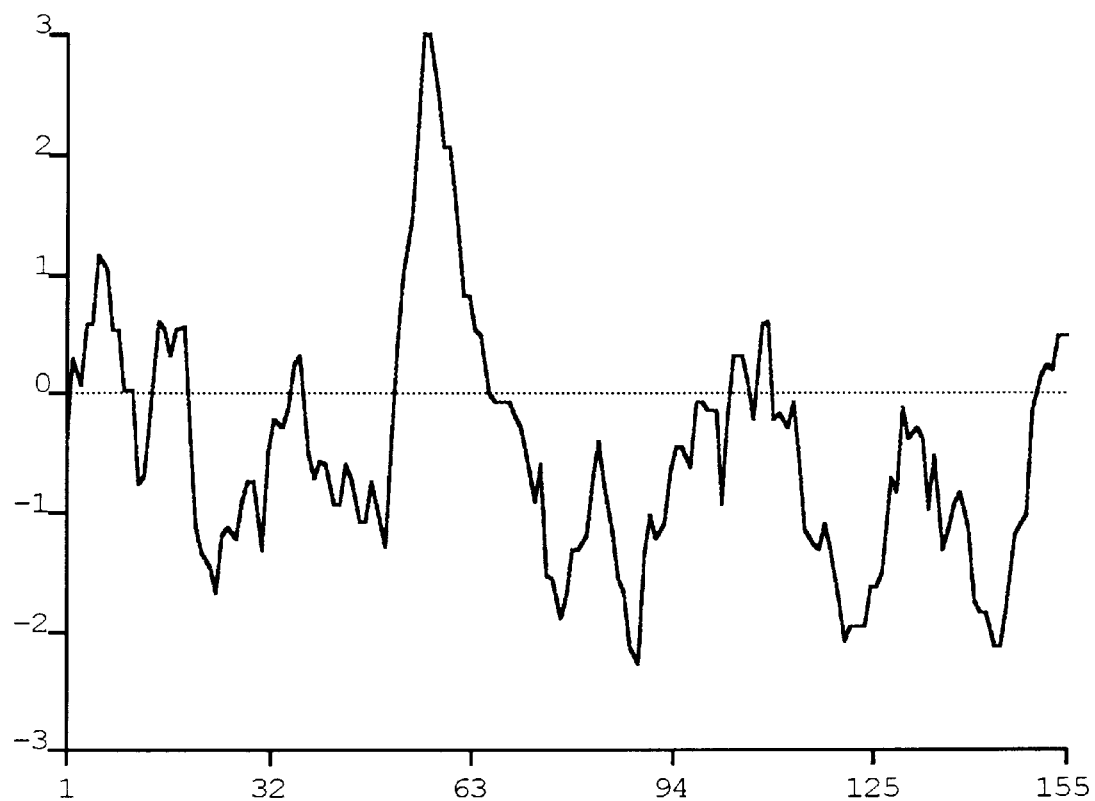
FIGS. 7A and 7B show the hydrophobicity plots for VMP2 (SEQ ID NO:3) and rat PMP22 (SEQ ID NO:9), respectively; the positive X axis reflects amino acid position, and the negative Y axis, hydrophobicity (MacDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

VMP, as used herein, refers to the amino acid sequences of substantially purified VMP obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to VMP, increases or prolongs the duration of the effect of VMP. Agonists may include proteins, nucleic acids, carbohydrates, or any other molecules which bind to and modulate the effect of VMP.

An "allele" or "allelic sequence", as used herein, is an alternative form of the gene encoding VMP. Alleles may result from at least one mutation in the nucleic acid sequence and may result in altered mnRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding VMP as used herein include those with deletions, insertions, or substitutions of different nucleotides resulting in a polynucleotide that encodes the same or a functionally equivalent VMP. Included within this definition are polymorphisms which may or may not be readily detectable using a particular oligonucleotide probe of the polynucleotide encoding VMP, and improper or unexpected hybridization to alleles, with a locus other than the normal chromosomal locus for the polynucleotide sequence encoding VMP. The encoded protein may also be "altered" and contain deletions, insertions, or substitutions of amino acid residues which produce a silent change and result in a functionally equivalent VMP. Deliberate amino acid substitutions may be made on the basis of similarity in polarity, charge, solubility, hydrophobicity, hydrophilicity, and/or the amphipathic nature of the residues as long as the biological or immunological activity of VMP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of VMP are preferably about 5 to about 15 amino acids in length and retain the biological activity or the immunological activity of VMP. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to VMP, decreases the amount or the duration of the effect of the biological or immunological activity of VMP. Antagonists may include proteins, nucleic acids, carbohydrates, antibodies or any other molecules which decrease the effect of VMP.

As used herein, the term "antibody" refers to intact molecules as well as fragments thereof, such as Fa, F(ab')$_2$, and Fv, which are capable of binding the epitopic determinant. Antibodies that bind VMP polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic VMP, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding VMP or fragments thereof may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2, SEQ ID NO:4, or SEQ ID NO:6, by northern analysis is indicative of the presence of niRNA encoding VMP in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to VMP or the encoded VMP. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat (Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of VMP. For example, modulation may cause an increase or a decrease in protein activity, binding characteristics, or any other biological, functional or immunological properties of VMP.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length VMP1 and fragments thereof, and a protein "comprising at least a portion of the amino acid sequence of SEQ ID NO:3" encompasses the full-length VMP2 and fragments thereof, and a protein "comprising at least a portion of the amino acid sequence of SEQ ID NO:5" encompasses the full-length VMP3 and fragments thereof.

The term "sample", as used herein, is used in its broadest sense. A biological sample suspected of containing nucleic acid encoding VMP, or fragments thereof, or VMP itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of VMP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of three new human vesicle membrane protein-like proteins, VMP (VMP1, VMP2, and VMP3), the polynucleotides encoding VMP, and the use of these compositions for the diagnosis, prevention, or treatment of developmental, vesicle trafficking, immunological, reproductive, and neoplastic disorders.

Nucleic acids encoding the VMP1 of the present invention were first identified in Incyte Clone 743725 from the brain cDNA library (BRAITUT01) using a computer search for amino acid sequence alignments. A consensus sequence, SEQ ID NO:2, was derived from the following overlapping and/or extended nucleic acid sequences: Incyte Clones 743725 (BRAITUT01), 2521256 (BRAITUT21), 602137 (BRSNOT02), 2373064 (ADRENOT07), 1732084 (BRSTUT08), 911226 (STOMNOT02), and 2226546 (SEMVNOT01).

In one embodiment, the invention encompasses a polypeptide comprising the amino acid sequence of SEQ ID NO:1, as shown in FIGS. 1A, 1B, and 1C. VMP is 214 amino acids in length and has two potential protein kinase A or G phosphorylation sites at residues S-34 and S-182, two potential casein kinase II phosphorylation sites at residues S-34 and S-127, and a predicted size of 22 kDa. As shown in FIGS. 4A and 4B, VMP1 has chemical and structural homology with C. boidinii PMP20 (GI170899; SEQ ID NO:7), and Synechocystis membrane protein s111621 (GI 1652858; SEQ ID NO:8). In particular, VMP1 and C. boidinii PMP20 share 29% identity, have one potential casein kinase II phosphorylation site, and have similar isoelectric points, 8.7 and 9.8, respectively. Northern analysis shows the expression of this sequence in various libraries, at least 57% of which are immortalized or cancerous and at least 25% of which involve immune response. Of particular note is the expression of VMP1 in gastrointestinal, lung, heart, breast, prostate, and brain tissues, in hematopoietic and smooth muscle tissues, and in fetal tissues.

Nucleic acids encoding the VMP2 of the present invention were first identified in Incyte Clone 1626663 from the colon poly cDNA library (COLNPOT01) using a computer search for amino acid sequence alignments. A consensus sequence, SEQ ID NO:4, was derived from the following overlapping and/or extended nucleic acid sequences: Incyte Clones 1626663 (COLNPOT01), 1833801 (BRAINON01), 226233 (PANCNOT01), 1258545 (MENITUT03), 2515523 (LIVRTUT04), and 1579696 (DUODNOT01).

Figure 7B:
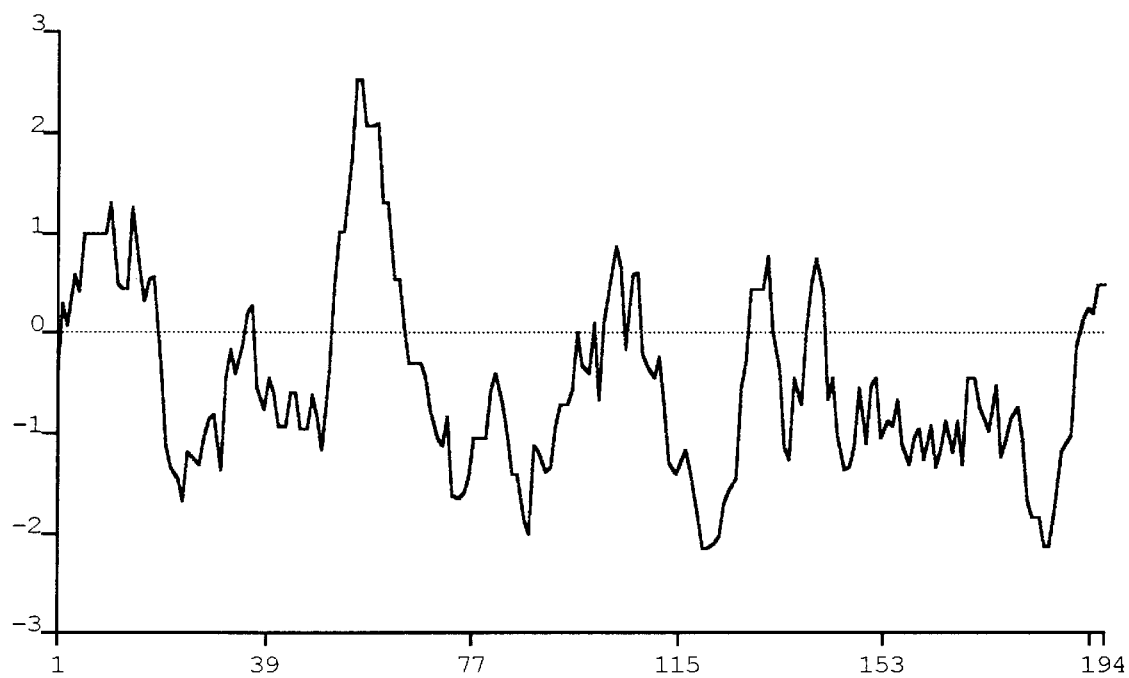

In one embodiment, the invention encompasses a polypeptide comprising the amino acid sequence of SEQ ID NO:3, as shown in FIGS. 2A and 2B. VMP2 is 155 amino acids in length, has a potential serine-pyruvate aminotransferase class-V pyridoxal-phosphate attachment site between residues M-1 and L-17 (a peroxisomal/mitochondrial localization signal), a potential lipocalin signature between residues N-63 and A-76 (found in C. boidinii peroxisomal integral membrane protein, PMP47), and a predicted size of 17.6 kDa. As shown in FIG. 5, VMP2 has chemical and structural homology with rat PMP22 (GI 297437; SEQ ID NO:9). In particular, VMP2 and rat PMP22 share 72% identity, the lipocalin signature, and have similar potential isoelectric points, 10.64 and 10.53, respectively. As illustrated by FIGS. 7A and 7B, VMP2 and rat PMP22 have rather similar hydrophobicity plots. Northern analysis shows the expression of this sequence in various libraries, at least 64% of which are immortalized or cancerous and at least 27% of which involve immune response. Of particular note is the expression of VMP2 in gastrointestinal, breast, prostate, and brain tissues, in hematopoietic tissue, and in fetal tissues.

Nucleic acids encoding the VMP3 of the present invention were first identified in Incyte Clone 2822412 from the adrenal pheochromocytoma cDNA library (ADRETUT06) using a computer search for amino acid sequence alignments. A consensus sequence, SEQ ID NO:6, was derived from the following overlapping and/or extended nucleic acid sequences: Incyte Clones 2822412 (ADRETUT06), 3236331 (COLNUCT03), 269777 (HNT2NOT01), 1359919 (LUNGNOT12), 1609872 (COLNTUT06), 770535 (COLNCRT01), 2505 (HMC1NOT01), 896216 (BRSTNOT05), 741936 (PANCNOT04), 2112041 (BRAITUT03), and 2132059 (OVARNOT03).

Figure 8A:
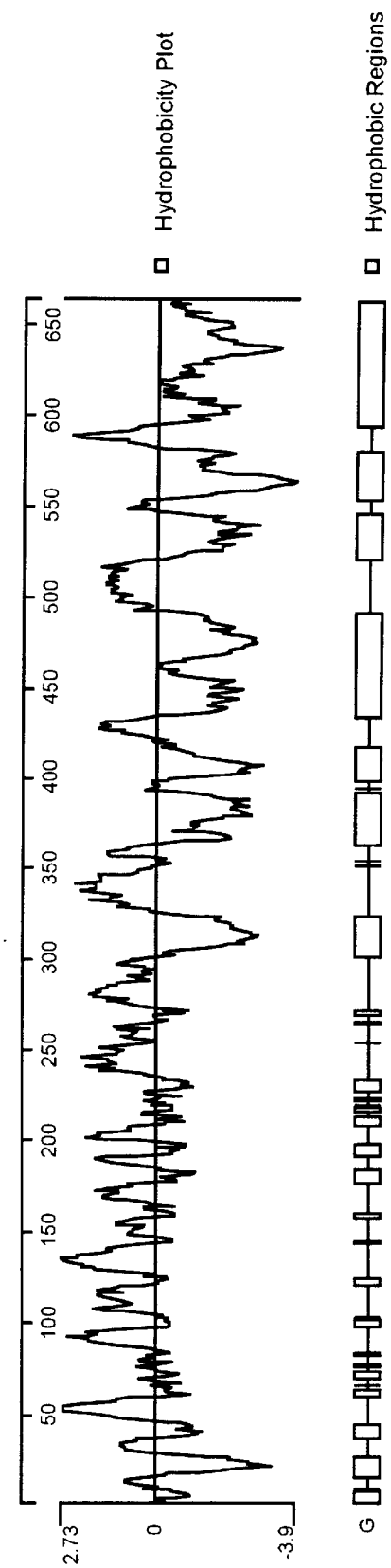
FIGS. 8A and 8B show the hydrophobicity plots for VMP3 (SEQ ID NO:5) and human KIAA0255 (SEQ ID NO:11), respectively; the positive X axis reflects amino acid position, and the negative Y axis, hydrophobicity, produced using the Protean protein analysis program of DNASTAR™ software (DNASTAR Inc, Madison Wis.).
Figure 8B:
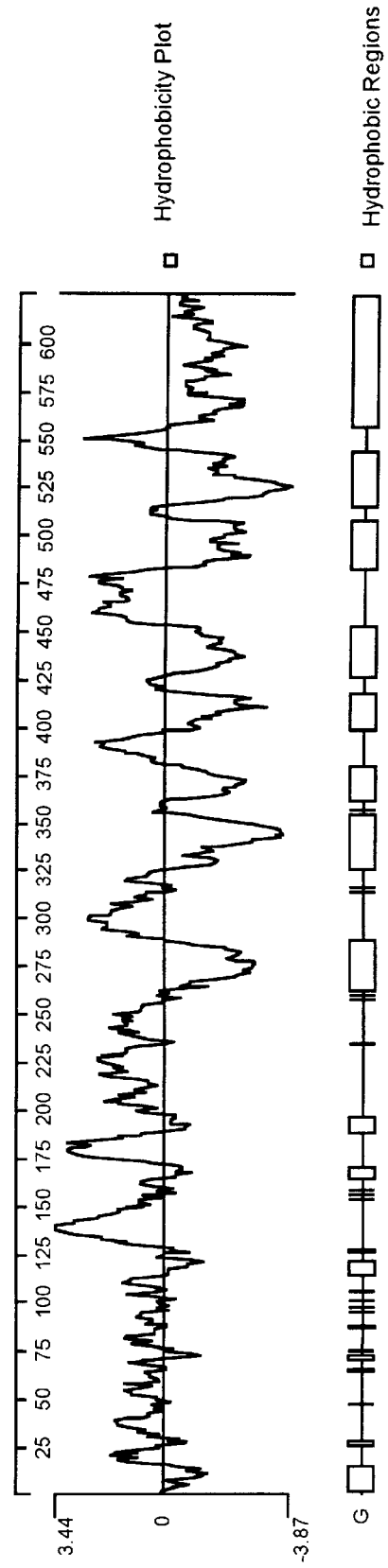

In one embodiment, the invention encompasses a polypeptide comprising the amino acid sequence of SEQ ID NO:5, as shown in FIGS. 3A, 3B, 3C, 3D, 3E, 3F, and 3G. VMP3 is 663 amino acids in length and has two potential protein kinase A or G phosphorylation sites at residues S-93 and T-119, six potential casein kinase II phosphorylation sites at residues T-79, T-243, S-274, S-285, S-338, and T-568, six potential protein kinase C phosphorylation sites at residues S-2, T-119, T-130, T-185, S-239, and S-258, one potential tyrosine kinase phosphorylation site at residue Y-517, ten potential hydrophobic transmembrane domains between residues R-15 and V-27, W-301 and R-324, L-364 and N-395, L-399 and F-421, L-435 and S-462, S-462 and Y-490, L-521 and 1–546, M-554 and L-581, L-594 and T-618, and T-618 and D-663, and a predicted size of 76 kDa. As shown in FIGS. 6A, 6B, 6C, and 6D, VMP3 has chemical and structural homology with human KIAA0255 (GI 1665777; SEQ ID NO:10) and yeast endosome EMP70 (p24a) (GI 2131246; SEQ ID NO:11). In particular, VMP3 and human KIAA0255 share 41% identity, one potential casein kinase II phosphorylation site, two potential protein kinase C phosphorylation sites, and one potential tyrosine kinase phosphorylation site. In addition, VMP3 and human KIAA0255 have similar potential isoelectric points, 7.1 and 6.2, respectively. As illustrated by FIGS. 8A and 8B, VMP3 and human KIAA0255 have rather similar hydrophobicity plots. Northern analysis shows the expression of this sequence in various libraries, at least 59% of which are immortalized or cancerous and at least 24% of which involve immune response. Of particular note is the expression of VMP3 in gastrointestinal, lung, breast, ovary, prostate, and brain tissues, in hematopoietic and smooth muscle tissues, and in fetal tissues.

The invention also encompasses VMP variants. A preferred VMP variant is one having at least 80%, and more preferably at least 90%, amino acid sequence identity to the VMP amino acid sequence and retaining at least one biological, immunological, or other functional characteristic or activity of VMP. A most preferred VMP variant is one having at least 95% amino acid sequence identity to SEQ ID NO:1, SEQ ID NO:3, or SEQ ID NO:5.

The invention also encompasses polynucleotides which encode VMP. Accordingly, any nucleic acid sequence which encodes the amino acid sequence of VMP can be used to produce recombinant molecules which express VMP. In a particular embodiment, the invention encompasses the polynucleotide comprising the nucleic acid sequence of SEQ ID NO:2 as shown in FIGS. 1A, 1B, and 1C. In another embodiment, the invention encompasses the polynucleotide comprising the nucleic acid sequence of SEQ ID NO:4 as shown in FIGS. 2A and 2B. In another embodiment, the invention encompasses the polynucleotide comprising the nucleic acid sequence of SEQ ID NO:6 as shown in FIGS. 3A, 3B, 3C, 3D, 3E, 3F, and 3G.

It will be appreciated by those skilled in the art that as a result of the degeneracy of the genetic code, a multitude of nucleotide sequences encoding VMP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring VMP, and all such variations are to be considered as being specifically disclosed.

Although nucleotide sequences which encode VMP and its variants are preferably capable of hybridizing to the nucleotide sequence of the naturally occurring VMP under appropriately selected conditions of stringency, it may be advantageous to produce nucleotide sequences encoding VMP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding VMP and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode VMP and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding VMP or any fragment thereof.

Also encompassed by the invention are polynucleotide sequences that are capable of hybridizing to the claimed nucleotide sequences, and in particular, those shown in SEQ ID NO:2, SEQ ID NO:4, or SEQ ID NO:6, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding VMP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68–°72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown figment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode VMP may be used in recombinant DNA molecules to direct expression of VMP, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express VMP.

As will be understood by those of skill in the art, it may be advantageous to produce VMP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter VMP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding VMP may be ligated to a heterologous sequence to encode a fusion protein. For example, to screen peptide libraries for inhibitors of VMP activity, it may be useful to encode a chimeric VMP protein that can be recognized by a commercially available antibody. A fusion protein may also be engineered to contain a cleavage site located between the VMP encoding sequence and the heterologous protein sequence, so that VMP may be cleaved and purified away from the heterologous moiety.

In another embodiment, sequences encoding VMP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of VMP, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of VMP, or any part thereof, may be altered during direct synthesis and/or combined using chemical methods with sequences from other proteins, or any part thereof, to produce a variant polypeptide.

In order to express a biologically active VMP, the nucleotide sequences encoding VMP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding VMP and appropriate transcriptional and translational control elements. These methods include in vitro recombinant DNA techniques, synthetic techniques, and in vivo genetic recombination. Such techniques are described in Sanbrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding VMP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding VMP, vectors based on SV40 or EBV may be used with an appropriate selectable marker.

In bacterial systems, a number of expression vectors may be selected depending upon the use intended for VMP. For example, when large quantities of VMP are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding VMP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding VMP may be driven by any of a number of promoters. For example, viral promoters such as the 35S and 19S promoters of CaMV may be used alone or in combination with the omega leader sequence from TMV (Takamatsu, N. (1987) *EMBO J.* 6:307–311). Alternatively, plant promoters such as the small subunit of RUBISCO or heat shock promoters may be used (Coruzzi, G. et al. (1984) *EMBO J.* 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express VMP. For example, in one such system, *Autographa californica* nuclear polyhedrosis virus (AcNPV) is used as a vector to express foreign genes in *Spodoptera frugiperda* cells or in Trichoplusia larvae. The sequences encoding VMP may be cloned into a non-essential region of the virus, such as the polyhedrin gene, and placed under control of the polyhedrin promoter. Successful insertion of VMP will render the polyhedrin gene inactive and produce recombinant virus lacking coat protein. The recombinant viruses may then be used to infect, for example, *S. fugiperda* cells or Trichoplusia larvae in which VMP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding VMP may be ligated into an adenovirus tanscription/translation complex consisting of the late promoter and tripartite leader sequence. Insertion in a non-essential E1 or E3 region of the viral genome may be used to obtain a viable virus which is capable of expressing VMP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding VMP. Such signals include the ATG initiation codon and adjacent sequences. In cases where sequences encoding VMP, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express VMP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$or $aprt^-$cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding VMP is inserted within a marker gene sequence, transformed cells containing sequences encoding VMP can be identified by the absence of marker gene function. Alternatively, a marker gene can be placed in tandem with a sequence encoding VMP under the control of a single promoter. Expression of the marker gene in response to induction or selection usually indicates expression of the tandem gene as well.

Alternatively, host cells which contain the nucleic acid sequence encoding VMP and express VMP may be identified by a variety of procedures known to those of skill in the art. These procedures include, but are not limited to, DNA- DNA or DNA-RNA hybridizations and protein bioassay or immunoassay techniques which include membrane, solution, or chip based technologies for the detection and/or quantification of nucleic acid or protein.

The presence of polynucleotide sequences encoding VMP can be detected by DNA-DNA or DNA-RNA hybridization or amplification using probes or fragments or fragments of polynucleotides encoding VMP. Nucleic acid amplification based assays involve the use of oligonucleotides or oligomers based on the sequences encoding VMP to detect transformants containing DNA or RNA encoding VMP.

A variety of protocols for detecting and measuring the expression of VMP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on VMP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding VMP include oligolabeling, nick translation, end-labeling or PCR amplification using a labeled nucleotide. Alternatively, the sequences encoding VMP, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding VMP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode VMP may be designed to contain signal sequences which direct secretion of VMP through a prokaryotic or eukaryotic cell membrane. Other constructions may be used to join sequences encoding VMP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and VMP may be used to facilitate purification. One such expression vector provides for expression of a fusion protein containing VMP and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif 3: 263–281) while the enterokinase cleavage site provides a means for purifying VMP from the fusion protein. A discussion of vectors which contain fusion proteins is provided in Kroll, D. J. et al. (1993; DNA Cell Biol. 12:441–453).

In addition to recombinant production, fragments of VMP may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of VMP may be chemically synthesized separately and combined using chemical methods to produce the full length molecule.

THERAPEUTICS

Chemical and structural homology exists among VMP1, *C. boidinii* PMP20 (GI 170899; SEQ ID NO:7), and Synechocystis membrane protein s111621 (GI 1652858; SEQ ID NO:8). In addition, VMP1 is expressed in gastrointestinal, lung, heart, breast, prostate, and brain tissues, in hematopoietic and smooth muscle tissues, and in fetal tissues. Therefore, VMP1 appears to play a role in developmental, vesicle trafficking, immunological, reproductive, and neoplastic disorders.

Chemical and structural homology exists between VMP2 and rat PMP22 (GI 297437; SEQ ID NO:9). In addition, VMP2 is expressed in gastrointestinal, breast, prostate, and brain tissues, in hematopoietic tissue, and in fetal tissues. Therefore, VMP2 appears to play a role in developmental, vesicle trafficking, immunological, reproductive, and neoplastic disorders.

Chemical and structural homology exists among VMP3 and human KIAA0255 (GI 1665777; SEQ ID NO:10) and yeast endosome EMP70 (p24a) (GI 2131246; SEQ ID NO:11). In addition, VMP3 is expressed in gastrointestinal, lung, breast, ovary, prostate, and brain tissues, in hematopoietic and smooth muscle tissues, and in fetal tissues. Therefore, VMP3 appears to play a role in developmental, vesicle trafficking, immunological, reproductive, and neoplastic disorders.

In one embodiment, VMP or a fragment or derivative thereof may be administered to a subject to treat or prevent a developmental disorder. The term "developmental disorder" refers to any disorder associated with development or function of a tissue, organ, or system of a subject (such as the brain, adrenal gland, kidney, skeletal or reproductive system). Such disorders include, but are not limited to, renal tubular acidosis, anemia, Cushing's syndrome, achondroplastic dwarfism, Duchenne and Becker muscular dystrophy, epilepsy, gonadal dysgenesis, WAGR syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, congenital glaucoma, cataract, and sensorineural hearing loss.

In another embodiment, a vector capable of expressing VMP, or a fragment or a derivative thereof, may also be administered to a subject to treat or prevent a developmental disorder including, but not limited to, those described above.

In still another embodiment, an agonist of VMP may also be administered to a subject to treat or prevent a developmental disorder including, but not limited to, those described above.

In one embodiment, VMP or a fragment or derivative thereof may be administered to a subject to treat or prevent a vesicle trafficking disorder. Such disorders include, but are not limited to, cystic fibrosis, glucose-galactose malabsorption syndrome, hypercholesterolemia, diabetes mellitus, diabetes insipidus, hyper- and hypoglycemia, Grave's disease, goiter, Cushing's disease, and Addison's disease; gastrointestinal disorders including ulcerative colitis and gastric and duodenal ulcers; other conditions associated with abnormal vesicle trafficking, including AIDS; allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; Zellweger syndrome; rhizomelic chonrodysplasia punctata; X-linked adrenoleukodystrophy; acyl-CoA oxidase deficiency; bifunctional enzyme deficiency; classical Refsum's disease; DHAP alkyl transferase deficiency; acatalasemia; systemic lupus erythematosus; toxic shock syndrome; traumatic tissue damage; and viral, bacterial, fungal, helminth, and protozoal infections.

In another embodiment, a vector capable of expressing VMP, or a fragment or a derivative thereof, may also be administered to a subject to treat or prevent a vesicle trafficking disorder including, but not limited to, those described above.

In still another embodiment, an agonist of VMP may also be administered to a subject to treat or prevent a vesicle trafficking disorder including, but not limited to, those described above.

In one embodiment, an antagonist of VMP may be administered to a subject to prevent or treat an immunological disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, and extracorporeal circulation; viral, bacterial, fungal, parasitic, protozoal, and helminthic infections; and trauma In one aspect, an antibody which specifically binds VMP may be used directly as an antagonist or indirectly as a targeting or delivery mechanism for bringing a pharmaceutical agent to cells or tissue which express VMP.

In another embodiment, a vector expressing the complement of the polynucleotide encoding VMP may be administered to a subject to treat or prevent an immunological disorder including, but not limited to, those described above.

In one embodiment, an antagonist of VMP may be administered to a subject to prevent or treat a reproductive disorder. Such disorders may include, but are not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, and prostatitis; and carcinoma of the male breast and gynecomastia. In one aspect, an antibody which specifically binds VMP may be used directly as an antagonist or indirectly as a targeting or delivery mechanism for bringing a pharmaceutical agent to cells or tissue which express VMP.

In another embodiment, a vector expressing the complement of the polynucleotide encoding VMP may be administered to a subject to treat or prevent a reproductive disorder including, but not limited to, those described above.

In one embodiment, an antagonist of VMP may be administered to a subject to prevent or treat a neoplastic disorder. Such disorders may include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, aii antibody which specifically binds VMP may be used directly as an antagonist or indirectly as a targeting or delivery mechanism for bringing a pharmaceutical agent to cells or tissue which express VMP.

In another embodiment, a vector expressing the complement of the polynucleotide encoding VMP may be administered to a subject to treat or prevent a neoplastic disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of VMP may be produced using methods which are generally known in the art. In particular, purified VMP may be used to produce antibodies or to screen libraries of pharmaceutical agents to identify those which specifically bind VMP.

Antibodies to VMP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with VMP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to VMP have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of VMP amino acids may be fused with those of another protein such as keyhole limpet hemocyanin and antibody produced against the chimeric molecule.

Monoclonal antibodies to VMP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce VMP-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for VMP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between VMP and its specific antibody. A two-site, monoclonal-based immunoassay utilizing monoclonal antibodies reactive to two non-interfering VMP epitopes is preferred, but a competitive binding assay may also be employed (Maddox, supra).

In another embodiment of the invention, the polynucleotides encoding VMP, or any fragment or complement thereof, may be used for therapeutic purposes. In one aspect, the complement of the polynucleotide encoding VMP may be used in situations in which it would be desirable to block the transcription of the rnRNA. In particular, cells may be transformed with sequences complementary to polynucleotides encoding VMP. Thus, complementary molecules or fragments may be used to modulate VMP activity, or to achieve regulation of gene function. Such technology is now well known in the art, and sense or antisense oligonucleotides or larger fragments, can be designed from various locations along the coding or control regions of sequences encoding VMP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding VMP. These techniques are described both in Sambrook et al. (supra) and in Ausubel et al. (supra).

Genes encoding VMP can be turned off by transforming a cell or tissue with expression vectors which express high levels of a polynucleotide or fragment thereof which encodes VMP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding VMP (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of MRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding VMP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding VMP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of VMP, antibodies to VMP, mimetics, agonists, antagonists, or inhibitors of VMP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of VMP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example VMP or fragments thereof, antibodies of VMP, agonists, antagonists or inhibitors of VMP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind VMP may be used for the diagnosis of conditions or diseases characterized by expression of VMP, or in assays to monitor patients being treated with VMP, agonists, antagonists or inhibitors. The antibodies useful for diagnostic purposes may be prepared in the same manner as those described above for therapeutics. Diagnostic assays for VMP include methods which utilize the antibody and a label to detect VMP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring VMP are known in the art and provide a basis for diagnosing altered or abnormal levels of VMP expression. Normal or standard values for VMP expression are established by combining body fluids or cell extracts taken from normal mammalian subjects, preferably human, with antibody to VMP under conditions suitable for complex formation The amount of standard complex formation may be quantified by various methods, but preferably by photometric, means. Quantities of VMP expressed in subject, control and disease, samples from biopsied tissues are compared with the standard values. Deviation between standard and subject values establishes the parameters for diagnosing disease.

In another embodiment of the invention, the polynucleotides encoding VMP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of VMP may be correlated with disease. The diagnostic assay may be used to distinguish between absence, presence, and excess expression of VMP, and to monitor regulation of VMP levels during therapeutic intervention.

In one aspect, hybridization with PCR probes which are capable of detecting polynucleotide sequences, including genomic sequences, encoding VMP or closely related molecules, may be used to identify nucleic acid sequences which encode VMP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding VMP, alleles, or related sequences.

Probes may also be used for the detection of related sequences, and should preferably contain at least 50% of the nucleotides from any of the VMP encoding sequences. The hybridization probes of the subject invention may be DNA or RNA and derived from the nucleotide sequence of SEQ ID NO:2, SEQ ID NO:4, or SEQ ID NO:6 or from genomic sequence including promoter, enhancer elements, and introns of the naturally occurring VMP.

Means for producing specific hybridization probes for DNAs encoding VMP include the cloning of nucleic acid sequences encoding VMP or VMP derivatives into vectors for the production of mRNA probes. Such vectors are known in the art, commercially available, and may be used to synthesize RNA probes m vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding VMP may be used for the diagnosis of conditions or disorders which are associated with expression of VMP. Examples of such conditions or disorders include a developmental disorder such as renal tubular acidosis, anemia, Cushing's syndrome, achondroplastic dwarfism, Duchenne and Becker muscular dystrophy, epilepsy, gonadal dysgenesis, WAGR syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, congenital glaucoma, cataract, and sensorineural hearing loss; a vesicle trafficking disorder such as cystic fibrosis, glucose-galactose malabsorption syndrome, hypercholesterolemia, diabetes mellitus, diabetes insipidus, hyper- and hypoglycemia, Grave's disease, goiter, and Addison's disease; gastrointestinal disorders including ulcerative colitis and gastric and duodenal ulcers; other conditions associated with abnormal vesicle trafficking, including AIDS; allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; Zellweger syndrome; rhizomelic chonrodysplasia punctata; X-linked adrenoleukodystrophy; acyl-CoA oxidase deficiency; bifunctional enzyme deficiency; classical Refsum's disease; DHAP alkyl transferase deficiency; acatalasemia; systemic lupus erythematosus; toxic shock syndrome; traumatic tissue damage; and viral, bacterial, fungal, helminth, and protozoal infections; an immunological disorder such as AIDS, Addison's disease, adult respiratory distress syndrome, anemia, atherosclerosis, bronchitis, cholecystitis, Crohn's disease, atopic dermatitis, dermatomyositis, emphysema, erythema nodosum, atrophic gastritis, gout, hypereosinophilia, irritable bowel syndrome, myocardial or pericardial inflammation, osteoporosis, pancreatitis, polymyositis, Werner syndrome, and autoimmune thyroiditis; complications of cancer, hemodialysis, and extracorporeal circulation; and trauma; a reproductive disorder such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, and prostatitis; and carcinoma of the male breast and gynecomastia; and a neoplastic disorder such as adenocarcinoma, leukemia, lymphoma, melanoma, myeloma, sarcoma, teratocarcinoma, and, in particular, cancers of the adrenal gland, bladder, bone, bone marrow, brain, cervix, gall bladder, ganglia, gastrointestinal tract, heart, kidney, liver, lung, muscle, pancreas, parathyroid, penis, salivary glands, skin, spleen, thymus, thyroid, and uterus. The polynucleotide sequences encoding VMP may be used in Southern or northern analysis, dot blot, or other membrane-based technologies; in PCR technologies; or in dipstick, pin, ELISA assays or microarrays utilizing fluids or tissues from patient biopsies to detect altered VMP expression. Such qualitative or quantitative methods are well known in the art.

In a particular aspect, the nucleotide sequences encoding VMP may be useful in assays that detect activation or induction of various cancers, particularly those mentioned above. The nucleotide sequences encoding VMP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding VMP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of VMP, a normal or standard profile for expression is established. This may be accomplished by combining body fluids or cell extracts taken from normal subjects, either animal or human, with a sequence, or a fragment thereof, which encodes VMP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding VMP may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of VMP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode VMP may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding VMP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, VMP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between VMP and the agent being tested, may be measured.

Another technique for drug screening which may be used provides for high throughput screening of compounds having suitable binding affinity to the protein of interest as described in published PCT application WO84/03564. In this method, as applied to VMP large numbers of different small test compounds are synthesized on a solid substrate, such as plastic pins or some other surface. The test compounds are reacted with VMP, or fragments thereof, and washed. Bound VMP is then detected by methods well known in the art. Purified VMP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding VMP specifically compete with a test compound for binding VMP. In this manner, the antibodies can be used to detect the presence of any peptide which shares one or more antigenic determinants with VMP.

In additional embodiments, the nucleotide sequences which encode VMP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

BRAITUT01

The BRAITUT01 cDNA library was constructed from brain tumor tissue (left frontal lobe) removed from a 50-year-old female Caucasian (lot #0089; Mayo Clinic, Rochester, Minn.) by brain lobectomy. The pathology report indicated recurrent grade 3 oligoastrocytoma with focal necrosis and extensive calcification. In 1986, the patient's brain had been irradiated with a total dose of 5082 cyg (Fraction 8). The patient family history included a brain tumor in a maternal uncle. Prior to surgery, the patient had disturbed speech and seizures that were being treated with Tegretoll (cabamazepine; Ciba-Geigy Corp., Summit N.J.). There was also a history of continuous tobacco abuse.

The frozen tissue was homogenized and lysed using a Brinkmann Homogenizer Polytron-PT 3000 (Brinkmann Instruments, Inc. Westbury, N.Y.) in guanidinium isothiocyanate solution. The lysate was extracted once with acid phenol at pH 4.0 per Stratagene's RNA isolation protocol (Stratagene Inc, San Diego Calif.). The lysate was re-extracted with phenol chloroform at pH 4.0. The RNA was then precipitated using 0.3 M sodium acetate and 2.5 volumes of ethanol, resuspended in DEPC-treated water and treated with DNase for 25 min at 37° C. Extraction and precipitation were repeated as before. The mRNA was isolated using the Qiagen Oligotex kit (QIAGEN Inc, Chatsworth Calif.) and used to construct the cDNA library.

COLNPOT01

The COLNPOT01 cDNA library was constructed from colon polyp tissue obtained from a 40-year-old Caucasian female (specimen #0251A, Mayo Clinic, Rochester, Minn.). The polyp was associated with an adenocarcinoma and was removed from the donor during colectomy. Pathology revealed multiple tubulovillous adenomas with low grade dysplasia situated predominately in the ascending and transverse colon forming flat, sessile and pedunculated masses. A focally invasive grade 2 adenocarcinoma had invaded the submucosa and an adenoma with high grade dysplasia was present in the transverse colon. Patient history included a benign neoplasm of the bowel, anemia, hypertension, adenotonsillectomy, and a total abdominal hysterectomy. At the time of surgery the patient was taking HCTZ and ferrous sulfate. Family history included hypertension and hyperlipidemia in the father and a malignant stomach neoplasm in a grandparent.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. Extraction and precipitation were repeated, and the mRNA was isolated using the Qiagen Oligotex kit (QIAGEN, Inc., Chatsworth, Calif.) and used to construct the cDNA library.

ADRETUT06

The ADRETUT06 cDNA library was constructed from tumorous adrenal tissue obtained from a 57-year-old Caucasian female (specimen #0298A) during an unilateral adrenalectomy. Pathology indicated pheochromocytoma, forming a nodular mass completely replacing the medulla of the adrenal. The surgical margins were uninvolved. The patient presented with nausea, vomiting and abdominal pain. Patient history included benign hypertension, cerebrovascular disease, diabetes type I, reflux esophagitis, and joint pain. Previous surgeries included an adenotonsillectomy, a spinal canal exploration, and a bilateral destruction of fallopian tubes. Patient medications included Humulin®, insulin, Daypro®, Zestril®, metoprolol tartrate, and phenoxybenzamine hydrochloride. Family history included benign hypertension in the mother, father, and a sibling; diabetes type I in the mother and a sibling; acute renal failure, and malignant skin lip neoplasm in the father; myocardial infarction in the mother; and primary tuberculous infection in a grandparent.

The frozen tissue was homogenized and lysed in Trizol reagent (1 g tissue/10 ml Trizol; Cat. #10296-028; GIBCO-BRL), a monoplastic solution of phenol and guanidine isothiocyanate, using a Brinkmann Homogenizer Polytron PT-3000 (Brinkmann Instruments, Westbury, N.Y.). After a brief incubation on ice, chloroform was added (1:5 v/v) and the lysate was centrifuged. The upper chloroform layer was removed to a fresh tube and the RNA extracted with isopropanol, resuspended in DEPC-treated water, and DNase treated for 25 min at 37° C. Extraction and precipitation were repeated as before. The mRNA was then isolated using the Qiagen Oligotex kit (QIAGEN, Inc., Chatsworth, Calif.) and used to construct the cDNA library.

The mRNAs from all three libraries were handled according to the recommended protocols in the SuperScript plasmid system (Cat. #18248-013, GIBCO-BRL). cDNA synthesis was initiated with a NotI-oligo d(T) primer. Double stranded cDNA was blunted, ligated to SalI (BRAITUT01) or EcoRI (COLNPOT01 and ADRETUT06) adaptors, digested with NotI, fractionated on a Sepharose CL4B column (Cat. #275105-01; Pharmacia), and cDNAs exceeding 400 bp were ligated into the NotI and SalI sites of the pSport I vector (BRAITUT01) or the NotI and EcoRI sites of the pINCY 1 vector (Incyte) (COLNPOT01 and ADRETUT06). The plasmid vector was subsequently transformed into DH5α™ competent cells (Cat. #18258-012; GIBCO-BRL).

II Isolation and Sequencing of cDNA Clones

Plasmid DNA was released from the cells and purified using the Miniprep kit (Catalog #77468; Advanced Genetic Technologies Corporation). The recommended protocol was employed except for the following changes: 1) the 96 wells were each filled with only 1 ml of sterile Terrific Broth (Catalog #22711, GIBCO-BRL) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R rotor at 2900 rpm for 5 minutes was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F. and Coulson A. R. (1975; J. Mol. Biol. 94:441f), using a Hamilton Micro Lab 2200 (Hamilton, Reno, Nev.) in combination with four Peltier Thermal Cyclers (PTC200 from MJ Research, Watertown, Mass.) and Applied Biosystems 377 or 373 DNA Sequencing Systems, and the reading frame was determined.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool; Altschul, S. F. (1993) J. Mol. Evol 36:290–300; Altschul, S. F. et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fuingal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases (mammalian (mamp), vertebrate (vrtp), and eukaryote (eukp)) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J.Mol.Evol. 36:290–300; Altschul, S. F. et al. (1990) J.Mol.Evol. 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding VMP occurs. Abundance and percent abundance are also reported. Abundance directly reflects the number of times a particular transcript is represented in a cDNA library, and percent abundance is abundance divided by the total number of sequences examined in the cDNA library.

V Extension of VMP Encoding Polynucleotides

The nucleic acid sequence of the Incyte Clones 743725, 1626663, or 2822412 were used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 40° C. (and holding) |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent *E. coli* cells (in 40 µl of appropriate media) were transformed with 3 µl of ligation mixture and cultured in 80 µl of SOC medium (Sambrook et al., supra). After incubation for one hour at 37° C., the *E. coli* mixture was plated on Luria Bertani (LB)-agar (Sambrook et al., supra) containing 2x Carb. The following day, several colonies were randomly picked from each plate and cultured in 150 µl of liquid LB/2x Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3x) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequences described herein are examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the VMP-encoding sequence, or any part thereof, is used to decrease or inhibit expression of naturally occurring VMP. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of VMP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the VMP-encoding transcript.

IX Expression of VMP

Expression of VMP is accomplished by subcloning the cDNAs into appropriate vectors and transforming the vectors into host cells. In this case, the cloning vector is also used to express VMP in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of VMP into the bacterial growth media which can be used directly in the following assay for activity.

X Demonstration of VMP Activity

VMP can be expressed in a mammalian cell line such as CHO by transforming with an eukaryotic expression vector encoding VMP. Eukaryotic expression vectors are commercially available, and the techniques to introduce them into cells are well known to those skilled in the art. The vesicular localization of VMP is examined using microscopy and a fluorescent antibody specific for extra-membrane portions of VMP. The number, arrangement, specificity, and pathway of vesicles containing VMP is examined. The search includes various cellular components such as ER, Golgi bodies, peroxisomes, endosomes, lysosomes, and the plasmalemma, and produces the information important to enhance vesicular processes in disease intervention, for example, in developmental abnormalities, and to disrupt vesicular processes in disease intervention, for example, in tumors.

XI Production of VMP Specific Antibodies

VMP that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6, is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring VMP Using Specific Antibodies

Naturally occurring or recombinant VMP is substantially purified by immunoaffinity chromatography using antibodies specific for VMP. An immunoaffinity column is constructed by covalently coupling VMP antibody to an activated chromatographic resin, such as CNBr-activated Sepharose (Pharmacia & Upjohn). After the coupling, the resin is blocked and washed according to the manufacturer's instructions.

Media containing VMP is passed over the immunoaffinity column, and the column is washed under conditions that allow the preferential absorbance of VMP (e.g., high ionic strength buffers in the presence of detergent). The column is eluted under conditions that disrupt antibody/VMP binding (eg, a buffer of pH 2–3 or a high concentration of a chaotrope, such as urea or thiocyanate ion), and VMP is collected.

XIII Identification of Molecules Which Interact with VMP

VMP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled VMP, washed and any wells with labeled VMP complex are assayed. Data obtained using different concentrations of VMP are used to calculate values for the number, affinity, and association of VMP with the candidate molecules.

All publications and patents mentioned in the above specification are herein incorporated by reference. Various modifications and variations of the described method and system of the invention will be apparent to those skilled in the art without departing from the scope and spirit of the invention- Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

```
                         SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 214 amino acids
        (B) TYPE: amino acid
        (C) STRANDEDNESS: single
        (D) TOPOLOGY: linear (vii) IMMEDIATE SOURCE:
        (A) LIBRARY: BRAITUT01
        (B) CLONE: 743725

(xi) SEQUENCE DESCRIPTION: SEQ ID NO:1:

Met Gly Leu Ala Gly Val Cys Ala Leu Arg Arg Ser Ala Gly Tyr Ile
 1               5                  10                  15

Leu Val Gly Gly Ala Gly Gly Gln Ser Ala Ala Ala Ala Ala Arg Arg
                20                  25                  30

Cys Ser Glu Gly Glu Trp Ala Ser Gly Gly Val Arg Ser Phe Ser Arg
            35                  40                  45

Ala Ala Ala Ala Met Ala Pro Ile Lys Val Gly Asp Ala Ile Pro Ala
        50                  55                  60

Val Glu Val Phe Glu Gly Glu Pro Gly Asn Lys Val Asn Leu Ala Glu
 65                  70                  75                  80

Leu Phe Lys Gly Lys Lys Gly Val Leu Phe Gly Val Pro Gly Ala Phe
                85                  90                  95

Thr Pro Gly Cys Ser Lys Thr His Leu Pro Gly Phe Val Glu Gln Ala
            100                 105                 110

Glu Ala Leu Lys Ala Lys Gly Val Gln Val Val Ala Cys Leu Ser Val
        115                 120                 125

Asn Asp Ala Phe Val Thr Gly Glu Trp Gly Arg Ala His Lys Ala Glu
    130                 135                 140

Gly Lys Val Arg Leu Leu Ala Asp Pro Thr Gly Ala Phe Gly Lys Glu
145                 150                 155                 160

Thr Asp Leu Leu Leu Asp Asp Ser Leu Val Ser Ile Phe Gly Asn Arg
                165                 170                 175

Arg Leu Lys Arg Phe Ser Met Val Val Gln Asp Gly Ile Val Lys Ala
            180                 185                 190

Leu Asn Val Glu Pro Asp Gly Thr Gly Leu Thr Cys Ser Leu Ala Pro
        195                 200                 205

Asn Ile Ile Ser Gln Leu
    210

(2) INFORMATION FOR SEQ ID NO:2:

(i) SEQUENCE CHARACTERISTICS:
```

(A) LENGTH: 993 base pairs
            (B) TYPE: nucleic acid
            (C) STRANDEDNESS: single
            (D) TOPOLOGY: linear (vii) IMMEDIATE SOURCE:
            (A) LIBRARY: BRAITUT01
            (B) CLONE: 743725

(xi) SEQUENCE DESCRIPTION: SEQ ID NO:2:

GTCGCCGCTG TGCCGCTAGC GGTGCCCCGC CTGCTGCGGT GGCACCAGCC AGGAGGGCCG      60

GGAAGTTGGG GAAAGGTTGG GGCCCGGTTG AGNGGGNCGG GGGGTTTAAA TTTGGGGGGC     120

GGCCCAGGCC CGCCTTCCGC AGGGTGTCGC CGCTGTGCCG CTAGCGGTGC CCCGCCTGCT     180

GCGGTGGCAC CAGCCAGGAG GCGGAGTGGA AGTGGCCGTG GGGCGGGTAT GGGACTAGCT     240

GGCGTGTGCG CCCTGAGACG CTCAGCGGGC TATATACTCG TCGGTGGGGC CGGCGGTCAG     300

TCTGCGGCAG CGGCAGCAAG ACGGTGCAGT GAAGGAGAGT GGGCGTCTGG CGGGGTCCGC     360

AGTTTCAGCA GAGCCGCTGC AGCCATGGCC CCAATCAAGG TGGGAGATGC CATCCCAGCA     420

GTGGAGGTGT TTGAAGGGGA GCCAGGGAAC AAGGTGAACC TGGCAGAGCT GTTCAAGGGC     480

AAGAAGGGTG TGCTGTTTGG AGTTCCTGGG GCCTTCACCC CTGGATGTTC AAGACACAC      540

CTGCCAGGGT TTGTGGAGCA GGCTGAGGCT CTGAAGGCCA AGGAGTCCA GGTGGTGGCC      600

TGTCTGAGTG TTAATGATGC CTTTGTGACT GGCGAGTGGG GCCGAGCCCA CAAGGCGGAA     660

GGCAAGGTTC GGCTCCTGGC TGATCCCACT GGGGCCTTTG GAAGGAGAC AGACTTATTA     720

CTAGATGATT CGCTGGTGTC CATCTTTGGG AATCGACGTC TCAAGAGGTT CTCCATGGTG     780

GTACAGGATG GCATAGTGAA GGCCCTGAAT GTGGAACCAG ATGGCACAGG CCTCACCTGC     840

AGCCTGGCAC CCAATATCAT CTCACAGCTC TGAGGCCCTG GGCCAGATTA CTTCCTCCAC     900

CCCTCCCTAT CTCACCTGCC CAGCCCTGTG CTGGGGCCCT GCAATTGGAA TGTTGGCCAG     960

ATTTCTGCAA TAAACACTTG TGGTTTGCGG CCA                                 993

(2) INFORMATION FOR SEQ ID NO:3:

(i) SEQUENCE CHARACTERISTICS:
            (A) LENGTH: 155 amino acids
            (B) TYPE: amino acid
            (C) STRANDEDNESS: single
            (D) TOPOLOGY: linear (vii) IMMEDIATE SOURCE:
            (A) LIBRARY: COLNPOT01
            (B) CLONE: 1626663

(xi) SEQUENCE DESCRIPTION: SEQ ID NO:3:

Met Ala Pro Ala Ala Ser Arg Leu Arg Ala Glu Ala Gly Leu Gly Ala
1               5                   10                  15

Leu Pro Arg Arg Ala Leu Ala Gln Tyr Leu Leu Phe Leu Arg Leu Tyr
                20                  25                  30

Pro Val Leu Thr Lys Ala Ala Thr Ser Gly Ile Leu Ser Ala Leu Gly
            35                  40                  45

Asn Phe Leu Ala Gln Met Ile Glu Lys Lys Lys Lys Glu Asn Ser
        50                  55                  60

Arg Ser Leu Asp Val Gly Gly Pro Leu Arg Tyr Ala Val Tyr Gly Phe
65                  70                  75                  80

Phe Phe Thr Gly Pro Leu Ser His Phe Phe Tyr Phe Phe Met Glu His
                85                  90                  95

Trp Ile Pro Pro Glu Val Pro Leu Ala Gly Leu Arg Arg Leu Leu Leu

```
            100                 105                 110
Asp Arg Leu Val Phe Ala Pro Ala Phe Leu Met Leu Phe Phe Leu Ile
            115                 120                 125

Met Asn Phe Leu Glu Phe Arg Val Leu Phe Ala Asn Leu Ala Ala Leu
    130                 135                 140

Phe Trp Tyr Ala Tyr Leu Ala Ser Leu Gly Lys
145                 150                 155
```

(2) INFORMATION FOR SEQ ID NO:4:

(i) SEQUENCE CHARACTERISTICS:
        (A) LENGTH: 800 base pairs
        (B) TYPE: nucleic acid
        (C) STRANDEDNESS: single
        (D) TOPOLOGY: linear (vii) IMMEDIATE SOURCE:
        (A) LIBRARY: COLNPOT01
        (B) CLONE: 1626663

(xi) SEQUENCE DESCRIPTION: SEQ ID NO:4:

```
GGTGCCCCCG GCGGCACGGC GCTGCGGCTC GAGGGAGGCG ATGGCGCCGG CCGCGTCCAG    60
GCTGCGGGCC GAAGCCGGGC TCGGGGCGCT GCCGCGGCGG GCGCTCGCCC AGTACTTGCT   120
CTTCCTGCGG CTCTACCCGG TGCTCACCAA GGCGGCCACC AGTGGCATTT TGTCAGCACT   180
TGGGAACTTC CTGGCCCAGA TGATTGAGAA GAAGCGGAAA AAAGAAAACT CTAGAAGTCT   240
GGATGTCGGT GGGCCTCTGA GATATGCCGT TTACGGGTTC TTCTTCACAG GCCGCTGAG    300
TCACTTCTTC TACTTCTTCA TGGAACATTG GATCCCTCCT GAGGTCCCCC TGGCAGGGCT   360
CAGGAGGCTT CTCCTGGACC GCCTCGTCTT TGCACCGGCC TTCCTCATGT TGTTCTTCCT   420
CATCATGAAC TTTCTGGAGT TCCGGGTGCT CTTCGCCAAC CTGGCAGCTC TGTTCTGGTA   480
TGCCTACCTG GCCTCCTTGG GGAAGTGACG ACCGCTGGGA GAACATCAGG TGCACTGTGG   540
ACGTGGGTCT GGGGGTCTCA CCCGCCCAGC GAGAGCAGAA CCAATCCAGT CAGGATGTCA   600
CTGACTCTAA ATCAGGTGAT TCAAGATGCC CCAAAAATGA TGGATAGAGA ACAGAAATC    660
TCTGAATGTC AGAAACCCTG TCTTTTAAAA AGGCAGTCAC TGCCTTCAGG TGGTGCTGCC   720
CCAGAAACTT AAAATTTAGT CGAGGCAGTT TCAATTGTTA CTGTGGACCG AATTAGGATC   780
ACAATAAACG ATAATGGGTC                                                800
```

(2) INFORMATION FOR SEQ ID NO:5:

(i) SEQUENCE CHARACTERISTICS:
        (A) LENGTH: 663 amino acids
        (B) TYPE: amino acid
        (C) STRANDEDNESS: single
        (D) TOPOLOGY: linear (vii) IMMEDIATE SOURCE:
        (A) LIBRARY: ADRETUT06
        (B) CLONE: 2822412

(xi) SEQUENCE DESCRIPTION: SEQ ID NO:5:

```
Met Ser Ala Arg Leu Pro Val Leu Ser Pro Pro Arg Trp Pro Arg Leu
1               5                   10                  15

Leu Leu Leu Ser Leu Leu Leu Gly Ala Val Pro Gly Pro Arg Arg
            20                  25                  30

Ser Gly Ala Phe Tyr Leu Pro Gly Leu Ala Pro Val Asn Phe Cys Asp
            35                  40                  45

Glu Glu Lys Lys Ser Asp Glu Cys Lys Ala Glu Ile Glu Leu Phe Val
```

```
        50                    55                    60
Asn Arg Leu Asp Ser Val Glu Ser Val Leu Pro Tyr Glu Tyr Thr Ala
 65                      70                  75                  80

Phe Asp Phe Cys Gln Ala Ser Glu Gly Lys Arg Pro Ser Glu Asn Leu
                     85                  90                  95

Gly Gln Val Leu Phe Gly Glu Arg Ile Glu Pro Ser Pro Tyr Lys Phe
                    100                 105                 110

Thr Phe Asn Lys Lys Glu Thr Cys Lys Leu Val Cys Thr Lys Thr Tyr
                    115                 120                 125

His Thr Glu Lys Ala Glu Asp Lys Gln Lys Leu Glu Phe Leu Lys Lys
                    130                 135                 140

Ser Met Leu Leu Asn Tyr Gln His His Trp Ile Val Asp Asn Met Pro
145                 150                 155                 160

Val Thr Trp Cys Tyr Asp Val Glu Asp Gly Gln Arg Phe Cys Asn Pro
                    165                 170                 175

Gly Phe Pro Ile Gly Cys Tyr Ile Thr Asp Lys Gly His Ala Lys Asp
                    180                 185                 190

Ala Cys Val Ile Ser Ser Asp Phe His Glu Arg Asp Thr Phe Tyr Ile
                    195                 200                 205

Phe Asn His Val Asp Ile Lys Ile Tyr Tyr His Val Val Glu Thr Gly
                    210                 215                 220

Ser Met Gly Ala Arg Leu Val Ala Ala Lys Leu Glu Pro Lys Ser Phe
225                 230                 235                 240

Lys His Thr His Ile Asp Lys Pro Asp Cys Ser Gly Pro Pro Met Asp
                    245                 250                 255

Ile Ser Asn Lys Ala Ser Gly Glu Ile Lys Ile Ala Tyr Thr Tyr Ser
                    260                 265                 270

Val Ser Phe Glu Glu Asp Asp Lys Ile Arg Trp Ala Ser Arg Trp Asp
                    275                 280                 285

Tyr Ile Leu Glu Ser Met Pro His Thr His Ile Gln Trp Phe Ser Ile
                    290                 295                 300

Met Asn Ser Leu Val Ile Val Leu Phe Leu Ser Gly Met Val Ala Met
305                 310                 315                 320

Ile Met Leu Arg Thr Leu His Lys Asp Ile Ala Arg Tyr Asn Gln Met
                    325                 330                 335

Asp Ser Thr Glu Asp Ala Gln Glu Glu Phe Gly Trp Lys Leu Val His
                    340                 345                 350

Gly Asp Ile Phe Arg Pro Pro Arg Lys Gly Met Leu Leu Ser Val Phe
                    355                 360                 365

Leu Gly Ser Gly Thr Gln Ile Leu Ile Met Thr Phe Val Thr Leu Phe
                    370                 375                 380

Phe Ala Cys Leu Gly Phe Leu Ser Pro Ala Asn Arg Gly Ala Leu Met
385                 390                 395                 400

Thr Cys Ala Val Val Leu Trp Val Leu Leu Gly Thr Pro Ala Gly Tyr
                    405                 410                 415

Val Ala Ala Arg Phe Tyr Lys Ser Phe Gly Gly Glu Lys Trp Lys Thr
                    420                 425                 430

Asn Val Leu Leu Thr Ser Phe Leu Cys Pro Gly Ile Val Phe Ala Asp
                    435                 440                 445

Phe Phe Ile Met Asn Leu Ile Leu Trp Gly Glu Gly Ser Ser Ala Ala
                    450                 455                 460

Ile Pro Phe Gly Thr Leu Val Ala Ile Leu Ala Leu Trp Phe Cys Ile
465                 470                 475                 480
```

```
Ser Val Pro Leu Thr Phe Ile Gly Ala Tyr Phe Gly Phe Lys Lys Asn
                485                 490                 495

Ala Ile Glu His Pro Val Arg Thr Asn Gln Ile Pro Arg Gln Ile Pro
            500                 505                 510

Glu Gln Ser Phe Tyr Thr Lys Pro Leu Pro Gly Ile Ile Met Gly Gly
            515                 520                 525

Ile Leu Pro Phe Gly Cys Ile Phe Ile Gln Leu Phe Phe Ile Leu Asn
            530                 535                 540

Ser Ile Trp Ser His Gln Met Tyr Tyr Met Phe Gly Phe Leu Phe Leu
545                 550                 555                 560

Val Phe Ile Ile Leu Val Ile Thr Cys Ser Glu Ala Thr Ile Leu Leu
                565                 570                 575

Cys Tyr Phe His Leu Cys Ala Glu Asp Tyr His Trp Gln Trp Arg Ser
            580                 585                 590

Phe Leu Thr Ser Gly Phe Thr Ala Val Tyr Phe Leu Ile Tyr Ala Val
            595                 600                 605

His Tyr Phe Phe Ser Lys Leu Gln Ile Thr Gly Thr Ala Ser Thr Ile
            610                 615                 620

Leu Tyr Phe Gly Tyr Thr Met Ile Met Val Leu Ile Phe Phe Leu Phe
625                 630                 635                 640

Thr Gly Thr Ile Gly Phe Phe Ala Cys Phe Trp Phe Val Thr Lys Ile
                645                 650                 655

Tyr Ser Val Val Lys Val Asp
            660
```

(2) INFORMATION FOR SEQ ID NO:6:

(i) SEQUENCE CHARACTERISTICS:
        (A) LENGTH: 2805 base pairs
        (B) TYPE: nucleic acid
        (C) STRANDEDNESS: single
        (D) TOPOLOGY: linear (vii) IMMEDIATE SOURCE:
        (A) LIBRARY: ADRETUT06
        (B) CLONE: 2822412

(xi) SEQUENCE DESCRIPTION: SEQ ID NO:6:

```
GTTGCGGTCC GCTTCGGTTT CTGTTGCGGG ACCCGGGGTG TCTCCTAGCG CAACCGGAAC      60

TAGCCTTCTG GGGGCCGGCT TCCTTTATCT CTGGCGGCCT TGTAGTCGTC TCCGAGACTC     120

CCCACCCCTC CTTCCCTCTT GACCCCCTAG GTTTGATTGC CCTTTCCCCG AAACAACTAT     180

CATGAGCGCG AGGCTGCCGG TGTTGTCTCC ACCTCGGTGG CCGCGGCTGT TGCTGCTGTC     240

GCTGCTCCTG CTGGGGCGG TTCCTGGCCC GCGCCGGAGC GGCGCTTTCT ACCTGCCCGG     300

CCTGGCGCCC GTCAACTTCT GCGACGAAGA AAAAAAGAGC GACGAGTGCA AGGCCGAAAT     360

AGAACTATTT GTGAACAGAC TTGATTCAGT GGAATCAGTT CTTCCTTATG AATACACAGC     420

GTTTGATTTT TGCCAAGCAT CAGAAGGAAA GCGCCCATCT GAAAATCTTG GTCAGGTACT     480

ATTCGGGGAA AGAATTGAAC CTTCACCATA TAAGTTTACG TTTAATAAGA AGGAGACCTG     540

TAAGCTTGTT TGTACAAAAA CATACCATAC AGAGAAAGCT GAAGACAAAC AAAAGTTAGA     600

ATTCTTGAAA AAAGCATGT TATTGAATTA TCAACATCAC TGGATTGTGG ATAATATGCC     660

TGTAACGTGG TGTTACGATG TTGAAGATGG TCAGAGGTTC TGTAATCCTG GATTTCCTAT     720

TGGCTGTTAC ATTACAGATA AAGGCCATGC AAAAGATGCC TGTGTTATTA GTTCAGATTT     780

CCATGAAAGA GATACATTTT ACATCTTCAA CCATGTTGAC ATCAAAATAT ACTATCATGT     840
```

-continued

```
TGTTGAAACT GGGTCCATGG GAGCAAGATT AGTGGCTGCT AAACTTGAAC CGAAAAGCTT     900

CAAACATACC CATATAGATA AACCAGACTG CTCAGGGCCC CCCATGGACA TAAGTAACAA     960

GGCTTCTGGG GAGATAAAAA TTGCCTATAC TTACTCTGTT AGCTTCGAGG AAGATGATAA    1020

GATCAGATGG GCGTCTAGAT GGACTATAT TCTGGAGTCT ATGCCTCATA CCCACATTCA     1080

GTGGTTTAGC ATTATGAATT CCCTGGTCAT TGTTCTCTTC TTATCTGGAA TGGTAGCTAT    1140

GATTATGTTA CGGACACTGC ACAAAGATAT TGCTAGATAT AATCAGATGG ACTCTACGGA    1200

AGATGCCCAG GAAGAATTTG GCTGGAAACT TGTTCATGGT GATATATTCC GTCCTCCAAG    1260

AAAAGGGATG CTGCTATCAG TCTTTCTAGG ATCCGGGACA CAGATTTTAA TTATGACCTT    1320

TGTGACTCTA TTTTTCGCTT GCCTGGGATT TTTGTCACCT GCCAACCGAG GAGCGCTGAT    1380

GACGTGTGCT GTGGTCCTGT GGGTGCTGCT GGGCACCCCT GCAGGCTATG TTGCTGCCAG    1440

ATTCTATAAG TCCTTTGGAG GTGAGAAGTG GAAAACAAAT GTTTTATTAA CATCATTTCT    1500

TTGTCCTGGG ATTGTATTTG CTGACTTCTT TATAATGAAT CTGATCCTCT GGGGAGAAGG    1560

ATCTTCAGCA GCTATTCCTT TTGGGACACT GGTTGCCATA TTGGCCCTTT GGTTCTGCAT    1620

ATCTGTGCCT CTGACGTTTA TTGGTGCATA CTTTGGTTTT AAGAAGAATG CCATTGAACA    1680

CCCAGTTCGA ACCAATCAGA TTCCACGTCA GATTCCTGAA CAGTCGTTCT ACACGAAGCC    1740

CTTGCCTGGT ATTATCATGG GAGGGATTTT GCCCTTTGGC TGCATCTTTA TACAACTTTT    1800

CTTCATTCTG AATAGTATTT GGTCACACCA GATGTATTAC ATGTTTGGCT TCCTATTTCT    1860

GGTGTTTATC ATTTTGGTTA TTACCTGTTC TGAAGCAACT ATACTTCTTT GCTATTTCCA    1920

CCTATGTGCA GAGGATTATC ATTGGCAATG GCGTTCATTC CTTACGAGTG GCTTTACTGC    1980

AGTTTATTTC TTAATCTATG CAGTACACTA CTTCTTTTCA AAACTGCAGA TCACGGGAAC    2040

AGCAAGCACA ATTCTGTACT TTGGTTATAC CATGATAATG GTTTTGATCT TCTTTCTTTT    2100

TACAGGAACA ATTGGCTTCT TTGCATGCTT TTGGTTTGTT ACCAAAATAT ACAGTGTGGT    2160

GAAGGTTGAC TGAAGAAGTC CAGTGTGTCC AGTTAAAACA GAAATAAATT AAACTCTTCA    2220

TCAACAAAGA CCTGTTTTTG TGACTGCCTT GAGTTTTATC AGAATTATTG GCCTAGTAAT    2280

CCTTCAGAAA CACCGTAATT CTAAATAAAC CTCTTCCCAT ACACCTTTCC CCCATAAGAT    2340

GTGTCTTCAA CACTATAAAG CATTTGTATT GTGATTTGAT TAAGTATATA TTTGGTTGTT    2400

CTCAATGAAG AGCAAATTTA AATATTATGT GCATTTGTAA ATACAGTAGC TATAAAATTT    2460

TCCATACTTC TAATGGCAGA ATAGAGGAGG CCATATTAAA TAATACTGAT GAAAGGCAGG    2520

ACACTGCATT GTAAATAGGA TTTTCTAGGC TCGGTAGGCA GAAAGAATTA TTTTTCTTTG    2580

AAGGAAATAA CTTTTTATCA TGGTAATTTT GAAGGATGAT TCCTATGATG TGTTCACCAG    2640

GGGAATGTGG CTTTTAAAGA AAATCTTCTA TTGGTTGTAA CTGTTCATAT CTTCTTACTT    2700

TTCTGTGTTG ACTTCATTAT TCCCATGGTA TTGGCCTTTT AAACTATGTG CCTCTGAGTC    2760

TTTCAATTTA TAAATTTGTT ATCTTAATAA ATATTATAAA AATGA                   2805
```

(2) INFORMATION FOR SEQ ID NO:7:

(i) SEQUENCE CHARACTERISTICS:
        (A) LENGTH: 167 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 170899

(xi) SEQUENCE DESCRIPTION: SEQ ID NO:7:

Met Ala Pro Ile Lys Arg Gly Asp Arg Phe Pro Thr Thr Asp Asp Val
1               5                   10                  15

Tyr Tyr Ile Pro Pro Glu Gly Gly Pro Gly Pro Leu Glu Leu Ser
                20                  25                  30

Lys Phe Val Lys Thr Lys Lys Phe Val Val Ser Val Pro Gly Ala
            35                  40                  45

Phe Thr Pro Pro Cys Thr Glu Gln His Leu Pro Gly Tyr Ile Lys Asn
    50                  55                      60

Leu Pro Arg Ile Leu Ser Lys Gly Val Asp Phe Val Leu Val Ile Ser
65                  70                  75                  80

Gln Asn Asp Pro Phe Val Leu Lys Gly Trp Lys Lys Glu Leu Gly Ala
                85                  90                  95

Ala Asp Ala Lys Lys Leu Val Phe Val Ser Asp Pro Asn Leu Lys Leu
                100                 105                 110

Thr Lys Lys Leu Gly Ser Thr Ile Asp Leu Ser Ala Ile Gly Leu Gly
            115                 120                 125

Thr Arg Ser Gly Arg Leu Ala Leu Ile Val Asn Arg Ser Gly Ile Val
130                 135                 140

Glu Tyr Ala Ala Ile Glu Asn Gly Gly Glu Val Asp Val Ser Thr Ala
145                 150                 155                 160

Gln Lys Ile Ile Ala Lys Leu
                165

(2) INFORMATION FOR SEQ ID NO:8:

(i) SEQUENCE CHARACTERISTICS:
        (A) LENGTH: 189 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1652858

(xi) SEQUENCE DESCRIPTION: SEQ ID NO:8:

Met Thr Pro Glu Arg Val Pro Ser Val Val Phe Lys Thr Arg Val Arg
1               5                   10                  15

Asp Glu Ser Val Pro Gly Pro Asn Pro Tyr Arg Trp Glu Asp Lys Thr
                20                  25                  30

Thr Glu Gln Ile Phe Gly Gly Lys Val Val Leu Phe Ser Leu Pro
            35                  40                  45

Gly Ala Phe Thr Pro Thr Cys Ser Ser Asn His Leu Pro Arg Tyr Glu
    50                  55                      60

Gln Leu Phe Glu Glu Phe Gln Ala Leu Gly Val Asp Asp Ile Ile Cys
65                  70                  75                  80

Leu Ser Val Asn Asp Ala Phe Val Met Phe Gln Trp Gly Lys Gln Ile
                85                  90                  95

Gly Ala Asp Lys Val Lys Leu Leu Pro Asp Gly Asn Gly Glu Phe Thr
                100                 105                 110

Arg Lys Met Gly Met Leu Val Glu Lys Ser Asn Leu Gly Phe Gly Met
            115                 120                 125

Arg Ser Trp Arg Tyr Ser Met Phe Val Asn Asp Gly Lys Ile Glu Lys
130                 135                 140

Met Phe Ile Glu Pro Glu Phe Gly Asp Asn Cys Pro Val Asp Pro Phe

```
                      145                 150                 155                 160
Glu Cys Ser Asp Ala Asp Thr Met Leu Ala Tyr Leu Lys Gly Ala Glu
                    165                 170                 175
Ala Pro Gly Val Ser Glu Pro Val Lys Ala Phe Val Gly
                180                 185

(2) INFORMATION FOR SEQ ID NO:9:

(i) SEQUENCE CHARACTERISTICS:
        (A) LENGTH: 194 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 297437

(xi) SEQUENCE DESCRIPTION: SEQ ID NO:9:

Met Ala Pro Ala Ala Ser Arg Leu Arg Val Glu Ser Glu Leu Arg Ser
 1               5                  10                  15
Leu Pro Lys Arg Ala Leu Ala Gln Tyr Leu Leu Phe Leu Lys Phe Tyr
                20                  25                  30
Pro Val Val Thr Lys Ala Val Ser Ser Gly Ile Leu Ser Ala Leu Gly
                35                  40                  45
Asn Leu Leu Ala Gln Met Ile Glu Lys Gln Lys Lys Asp Ser Arg
 50                  55                  60
Ser Leu Glu Val Ser Gly Leu Leu Arg Tyr Leu Val Tyr Gly Leu Phe
65                  70                  75                  80
Val Thr Gly Pro Leu Ser His Tyr Leu Tyr Leu Phe Met Glu Tyr Trp
                85                  90                  95
Val Pro Pro Glu Val Pro Trp Ala Arg Val Lys Arg Leu Leu Leu Asp
                100                 105                 110
Arg Leu Phe Phe Ala Pro Thr Phe Leu Leu Leu Phe Phe Phe Val Met
                115                 120                 125
Asn Leu Leu Glu Gly Lys Asn Ile Ser Val Phe Val Ala Lys Met Arg
                130                 135                 140
Ser Gly Phe Trp Pro Ala Leu Gln Met Asn Trp Arg Met Trp Thr Pro
145                 150                 155                 160
Leu Gln Phe Ile Asn Ile Asn Tyr Val Pro Leu Gln Phe Arg Val Leu
                165                 170                 175
Phe Ala Asn Met Ala Ala Leu Phe Trp Tyr Ala Tyr Leu Ala Ser Leu
                180                 185                 190
Gly Lys (2) INFORMATION FOR SEQ ID NO:10:

(i) SEQUENCE CHARACTERISTICS:
        (A) LENGTH: 625 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1665777

(xi) SEQUENCE DESCRIPTION: SEQ ID NO:10:

Met Cys Glu Thr Ser Ala Phe Tyr Val Pro Gly Val Ala Pro Ile Asn
 1               5                  10                  15
```

-continued

Phe His Gln Asn Asp Pro Val Glu Ile Lys Ala Val Lys Leu Thr Ser
                20                  25                  30

Ser Arg Thr Gln Leu Pro Tyr Glu Tyr Tyr Ser Leu Pro Phe Cys Gln
            35                  40                  45

Pro Ser Lys Ile Thr Tyr Lys Ala Glu Asn Leu Gly Glu Val Leu Arg
 50                  55                  60

Gly Asp Arg Ile Val Asn Thr Pro Phe Gln Val Leu Met Asn Ser Glu
 65                      70                  75                  80

Lys Lys Cys Glu Val Leu Cys Ser Gln Ser Asn Lys Pro Val Thr Leu
                    85                  90                  95

Thr Val Glu Gln Ser Arg Leu Val Ala Glu Arg Ile Thr Glu Asp Tyr
                100                 105                 110

Tyr Val His Leu Ile Ala Asp Asn Leu Pro Val Ala Thr Arg Leu Glu
            115                 120                 125

Leu Tyr Ser Asn Arg Asp Ser Asp Asp Lys Lys Glu Lys Asp Val
130                 135                 140

Gln Phe Glu His Gly Tyr Arg Leu Gly Phe Thr Asp Val Asn Lys Ile
145                 150                 155                 160

Tyr Leu His Asn His Leu Ser Phe Ile Leu Tyr Tyr His Arg Glu Asp
                165                 170                 175

Met Glu Glu Asp Gln Glu His Thr Tyr Arg Val Val Arg Phe Glu Val
                180                 185                 190

Ile Pro Gln Ser Ile Arg Leu Glu Asp Leu Lys Ala Asp Glu Lys Ser
            195                 200                 205

Ser Cys Thr Leu Pro Glu Gly Thr Asn Ser Ser Pro Gln Glu Ile Asp
    210                 215                 220

Pro Thr Lys Glu Asn Gln Leu Tyr Phe Thr Tyr Ser Val His Trp Glu
225                 230                 235                 240

Glu Ser Asp Ile Lys Trp Ala Ser Arg Trp Asp Thr Tyr Leu Thr Met
                245                 250                 255

Ser Asp Val Gln Ile His Trp Phe Ser Ile Ile Asn Ser Val Val Val
                260                 265                 270

Val Phe Phe Leu Ser Gly Ile Leu Ser Met Ile Ile Arg Thr Leu
    275                 280                 285

Arg Lys Asp Ile Ala Asn Tyr Asn Lys Glu Asp Asp Ile Glu Asp Thr
    290                 295                 300

Met Glu Glu Ser Gly Trp Lys Leu Val His Gly Asp Val Phe Arg Pro
305                 310                 315                 320

Pro Gln Tyr Pro Met Ile Leu Ser Ser Leu Leu Gly Ser Gly Ile Gln
                325                 330                 335

Leu Phe Cys Met Ile Leu Ile Val Ile Phe Val Ala Met Leu Gly Met
                340                 345                 350

Leu Ser Pro Ser Ser Arg Gly Ala Leu Met Thr Thr Ala Cys Phe Leu
            355                 360                 365

Phe Met Phe Met Gly Val Phe Gly Phe Ser Ala Gly Arg Leu Tyr
    370                 375                 380

Arg Thr Leu Lys Gly His Arg Trp Lys Lys Gly Ala Phe Cys Thr Ala
385                 390                 395                 400

Thr Leu Tyr Pro Gly Val Val Phe Gly Ile Cys Phe Val Leu Asn Cys
                405                 410                 415

Phe Ile Trp Gly Lys His Ser Ser Gly Ala Val Pro Phe Pro Thr Met
            420                 425                 430

Val Ala Leu Leu Cys Met Trp Phe Gly Ile Ser Leu Pro Leu Val Tyr

-continued

```
                435                 440                 445
Leu Gly Tyr Tyr Phe Gly Phe Arg Lys Gln Pro Tyr Asp Asn Pro Val
    450                 455                 460

Arg Thr Asn Gln Ile Pro Arg Gln Ile Pro Glu Gln Arg Trp Tyr Met
465                 470                 475                 480

Asn Arg Phe Val Gly Ile Leu Met Ala Gly Ile Leu Pro Phe Gly Ala
                485                 490                 495

Met Phe Ile Glu Leu Phe Phe Ile Phe Ser Ala Ile Trp Glu Asn Gln
                500                 505                 510

Phe Tyr Tyr Leu Phe Gly Phe Leu Phe Val Phe Ile Ile Leu Val
                515                 520                 525

Val Ser Cys Ser Gln Ile Ser Ile Val Met Val Tyr Phe Gln Leu Cys
    530                 535                 540

Ala Glu Asp Tyr Arg Trp Trp Trp Arg Asn Phe Leu Val Ser Gly Gly
545                 550                 555                 560

Ser Ala Phe Tyr Val Leu Val Tyr Ala Ile Phe Tyr Phe Val Asn Lys
                565                 570                 575

Leu Asp Ile Val Glu Phe Ile Pro Ser Leu Leu Tyr Phe Gly Tyr Thr
                580                 585                 590

Ala Leu Met Val Leu Ser Phe Trp Leu Leu Thr Gly Thr Ile Gly Phe
                595                 600                 605

Tyr Ala Ala Tyr Met Phe Val Arg Lys Ile Tyr Ala Ala Val Lys Ile
    610                 615                 620

Asp
625
```

(2) INFORMATION FOR SEQ ID NO:11:

(i) SEQUENCE CHARACTERISTICS:
        (A) LENGTH: 667 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 2131246

(xi) SEQUENCE DESCRIPTION: SEQ ID NO:11:

```
Met Ile Tyr Lys Met Ala His Val Gln Leu Leu Leu Tyr Phe Phe
1               5                   10                  15

Val Ser Thr Val Lys Ala Phe Tyr Leu Pro Gly Val Ala Pro Thr Thr
                20                  25                  30

Tyr Arg Glu Asn Asp Asn Ile Pro Leu Leu Val Asn His Leu Thr Pro
                35                  40                  45

Ser Met Asn Tyr Gln His Lys Asp Glu Asp Gly Asn Asn Val Ser Gly
    50                  55                  60

Asp Lys Glu Asn Phe Leu Tyr Ser Tyr Asp Tyr Tyr Asn Arg Phe
65                  70                  75                  80

His Phe Cys Gln Pro Glu Lys Val Glu Lys Gln Pro Glu Ser Leu Gly
                85                  90                  95

Ser Val Ile Phe Gly Asp Arg Ile Tyr Asn Ser Pro Phe Gln Leu Asn
                100                 105                 110

Met Leu Gln Glu Lys Glu Cys Glu Ser Leu Cys Lys Thr Val Ile Pro
                115                 120                 125

Gly Asp Asp Ala Lys Phe Ile Asn Lys Leu Ile Lys Asn Gly Phe Phe
    130                 135                 140
```

```
Gln Asn Trp Leu Ile Asp Gly Leu Pro Ala Ala Arg Glu Val Tyr Asp
145                 150                 155                 160

Gly Arg Thr Lys Thr Ser Phe Tyr Gly Ala Gly Phe Asn Leu Gly Phe
                165                 170                 175

Val Gln Val Thr Gln Gly Thr Asp Ile Glu Ala Thr Pro Lys Gly Ala
            180                 185                 190

Glu Thr Thr Asp Lys Asp Val Glu Leu Glu Thr Arg Asn Asp Arg Asn
        195                 200                 205

Met Val Lys Thr Tyr Glu Leu Pro Tyr Phe Ala Asn His Phe Asp Ile
    210                 215                 220

Met Ile Glu Tyr His Asp Arg Gly Gly Asn Tyr Arg Val Val Gly
225                 230                 235                 240

Val Ile Val Glu Pro Val Ser Ile Lys Arg Ser Ser Pro Gly Thr Cys
                245                 250                 255

Glu Thr Thr Gly Ser Pro Leu Met Leu Asp Gly Asn Asp Asn Glu
            260                 265                 270

Val Tyr Phe Thr Tyr Ser Val Lys Phe Asn Glu Ser Ala Thr Ser Trp
        275                 280                 285

Ala Thr Arg Trp Asp Lys Tyr Leu His Val Tyr Asp Pro Ser Ile Gln
290                 295                 300

Trp Phe Ser Leu Ile Asn Phe Ser Leu Val Val Val Leu Leu Ser Ser
305                 310                 315                 320

Val Val Ile His Ser Leu Leu Arg Ala Leu Lys Ser Asp Phe Ala Arg
                325                 330                 335

Tyr Asn Glu Leu Asn Leu Asp Asp Phe Gln Glu Asp Ser Gly Trp
            340                 345                 350

Lys Leu Asn His Gly Asp Val Phe Arg Ser Pro Ser Gln Ser Leu Thr
                355                 360                 365

Leu Ser Ile Leu Val Gly Ser Gly Val Gln Leu Phe Leu Met Val Thr
    370                 375                 380

Cys Ser Ile Phe Phe Ala Ala Leu Gly Phe Leu Ser Pro Ser Ser Arg
385                 390                 395                 400

Gly Ser Leu Ala Thr Val Met Phe Ile Leu Tyr Ala Leu Phe Gly Phe
                405                 410                 415

Val Gly Ser Tyr Thr Ser Met Gly Ile Tyr Lys Phe Phe Asn Gly Pro
            420                 425                 430

Tyr Trp Lys Ala Asn Leu Ile Leu Thr Pro Leu Leu Val Pro Gly Ala
        435                 440                 445

Ile Leu Leu Ile Ile Ile Ala Leu Asn Phe Phe Leu Met Phe Val His
450                 455                 460

Ser Ser Gly Val Ile Pro Ala Ser Thr Leu Phe Phe Met Val Phe Leu
465                 470                 475                 480

Trp Phe Leu Phe Ser Ile Pro Leu Ser Phe Ala Gly Ser Leu Ile Ala
                485                 490                 495

Arg Lys Arg Cys His Trp Asp Glu His Pro Thr Lys Thr Asn Gln Ile
            500                 505                 510

Ala Arg Gln Ile Pro Phe Gln Pro Trp Tyr Leu Lys Thr Ile Pro Ala
        515                 520                 525

Thr Leu Ile Ala Gly Ile Phe Pro Phe Gly Ser Ile Ala Val Glu Leu
    530                 535                 540

Tyr Phe Ile Tyr Thr Ser Leu Trp Phe Asn Lys Ile Phe Tyr Met Phe
545                 550                 555                 560
```

-continued

| | | | | | | | | | | | | |
|---|---|---|---|---|---|---|---|---|---|---|---|---|
|Gly|Phe|Leu|Phe|Phe<br>565|Ser|Phe|Leu|Leu<br>570|Thr|Leu|Thr|Ser<br>575|Ser|Leu|
|Val|Thr|Ile|Leu<br>580|Ile|Thr|Tyr|His|Ser<br>585|Leu|Cys|Leu|Glu|Asn<br>590|Trp|Lys|
|Trp|Gln|Trp<br>595|Arg|Gly|Phe|Ile|Ile<br>600|Gly|Gly|Ala|Gly|Cys<br>605|Ala|Leu|Tyr|
|Val|Phe|Ile|His<br>610|Ser|Ile|Leu|Phe<br>615|Thr|Lys|Phe|Lys<br>620|Leu|Gly|Gly|Phe|
|Thr|Thr|Ile|Val|Leu|Tyr|Val|Gly|Tyr|Ser|Ser|Val|Ile|Ser|Leu|Leu|
|625| | | | |630| | | |635| | | | | |640|
|Cys|Cys|Leu|Val|Thr<br>645|Gly|Ser|Ile|Gly|Phe<br>650|Ile|Ser|Ser|Met|Leu<br>655|Phe|
|Val|Arg|Lys|Ile|Tyr<br>660|Ser|Ser|Ile|Lys|Val<br>665|Asp|

What is claimed is:

1. An isolated and purified polynucleotide sequence encoding human vesicle membrane protein-like protein having the amino acid sequence of SEQ ID NO:3.

2. A composition comprising the polynucleotide sequence of claim 1.

3. An isolated and purified polynucleotide sequence which is complementary to the polynucleotide sequence of claim 1.

4. An isolated and purified polynucletide sequence comprising SEQ ID NO:4.

5. An isolated and purified polynucleotide sequence which is complementary to the polynucleotide sequence of claim 4.

6. An expression vector containing the polynucleotide sequence of claim 1.

7. A host cell containing the expression vector of claim 6.

8. A method for producing a polypeptide comprising the amino acid sequence of SEQ ID NO:3, the method comprising the steps of:

a) culturing the host cell of claim 7 under conditions suitable for the expression of the polypeptide; and b) recovering the polypeptide from the host cell culture.

9. A polynucleotide comprising a contiguous nucleotide sequence encoding amino acids 1 through 15 of SEQ ID NO:3 or the complement thereof.

10. A polynucleotide comprising a contiguous nucleotide sequence of nucleotides 1 through 87 of SEQ ID NO:4 or the complement thereof.

11. A polynucleotide comprising a contiguous nucleotide sequence of nucleotides 385 through 507 of SEQ ID NO:4 or the complement thereof.

12. A probe comprising 60 contiguous nucleotides of the polynucleotide of claim 10.

13. A probe comprising 60 contiguous nucleotides of the polynucleotide of claim 11.

14. A probe comprising 45 contiguous nucleotides encoding 15 contiguous amino acids of SEQ ID NO:3.

* * * * *